United States Patent [19]
Zaffaroni et al.

[11] Patent Number: 6,121,048
[45] Date of Patent: *Sep. 19, 2000

[54] METHOD OF CONDUCTING A PLURALITY OF REACTIONS

[76] Inventors: Alejandro C. Zaffaroni, 168 Isabella Ave., Atherton, Calif. 94025; Christopher J. Buchko, 418 High St., #2, Ann Arbor, Mich. 48104; Douglas N. Modlin, 4063 Scripps Ave., Palo Alto, Calif. 94306

[*] Notice: This patent issued on a continued prosecution application filed under 37 CFR 1.53(d), and is subject to the twenty year patent term provisions of 35 U.S.C. 154(a)(2).

[21] Appl. No.: 08/327,512

[22] Filed: Oct. 18, 1994

[51] Int. Cl.[7] .................................................. G01N 35/02
[52] U.S. Cl. ................................ 436/45; 436/94; 436/165
[58] Field of Search .................................. 422/62, 63, 64; 436/43, 45, 91, 94, 165

[56] References Cited

U.S. PATENT DOCUMENTS

| | | |
|---|---|---|
| 3,281,860 | 10/1966 | Adams et al. . |
| 3,710,933 | 1/1973 | Fulwlyer et al. ........................ 422/73 |
| 4,121,222 | 10/1978 | Diebold et al. . |
| 4,373,071 | 2/1983 | Itakura . |
| 4,458,066 | 7/1984 | Caruthers et al. . |
| 4,500,707 | 2/1985 | Caruthers et al. . |
| 4,728,502 | 3/1988 | Hamill .................................... 422/116 |
| 4,731,325 | 3/1988 | Palva et al. . |
| 4,780,504 | 10/1988 | Buendia et al. . |
| 4,812,512 | 3/1989 | Buendia et al. . |
| 4,877,745 | 10/1989 | Hayes et al. ............................. 436/166 |
| 4,992,383 | 2/1991 | Farnsworth . |
| 5,021,550 | 6/1991 | Zeiger . |
| 5,047,524 | 9/1991 | Andrus et al. . |
| 5,141,813 | 8/1992 | Nelson . |
| 5,143,854 | 9/1992 | Pirrung et al. .......................... 436/518 |
| 5,153,319 | 10/1992 | Caruthers et al. . |
| 5,256,549 | 10/1993 | Urdea . |
| 5,288,514 | 2/1994 | Ellman ........................................ 427/2 |
| 5,358,691 | 10/1994 | Clark et al. ............................... 422/63 |
| 5,677,195 | 10/1997 | Winkler et al. . |
| 5,698,393 | 12/1997 | Macioszek et al. . |
| 5,807,522 | 9/1998 | Brown et al. . |

FOREIGN PATENT DOCUMENTS

| | | |
|---|---|---|
| 0 260 965 | 3/1988 | European Pat. Off. . |
| 0417305 | 9/1990 | European Pat. Off. . |
| WO 89/10977 | 11/1989 | WIPO . |
| WO 90/00626 | 1/1990 | WIPO .............................. C12Q 1/68 |
| WO 90/03382 | 4/1990 | WIPO .............................. C07H 21/00 |
| WO 90/15070 | 12/1990 | WIPO .............................. C07K 1/04 |
| WO 92/10092 | 6/1992 | WIPO .............................. A01N 1/02 |
| WO 93/09668 | 5/1993 | WIPO . |
| WO 93/11262 | 6/1993 | WIPO . |

OTHER PUBLICATIONS

H. Mario Geysen et al., J. Immunological Methods 102 (1987) 259–274, Strategies for epitope analysis using peptide synthesis.

R.B. Merrifield, J. Am. Chem. Soc., 85 Jul. 20, 1963 2149–2154, Solid Phase Peptide Synthesis. I. The Synthesis of a Tetrapeptide.

Ohlmeyer, H.J., et al., Proc. Natl. Acad. Sci. USA, vol. 90, 10922–10926 (1993), "Complex Synthetic Chemical Libraries Indexed With Molecular Tags."

Tuerk, C., et al., Science, vol. 249, 505–510 (1990), "Systematic Evolution of Ligands by Exponential Enrichment: RNA Ligands to Bacteriophage T4 DNA Polymerase."

(List continued on next page.)

*Primary Examiner*—Lyle A. Alexander
*Attorney, Agent, or Firm*—Townsend and Townsend and Crew LLP

[57] ABSTRACT

An apparatus and method is provided for preparing and using a very large and diverse array of compounds on a substrate having rapidly accessible locations. The substrate contains cells in which the compounds of the array are located. Surrounding the cells is a non-wetable surface that prevents the solution in one cell from moving to adjacent cells. The compounds are delivered to the individual cells of the array by a micropipette attached to an X-Y translation stage.

20 Claims, 10 Drawing Sheets-

OTHER PUBLICATIONS

Needels, M.C., et al., *Proc. Natl. Acad. Sci. USA*, vol. 90, 10700–10704 (1993), "Generation and Screening of an Oligonucleotide–Encoded Synthetic Peptide Library."

Lam, K.S., et al., *Nature*, vol. 354, 82–84 (1991), "A New Type of Synthetic Peptide Library for Identifying Ligand–Binding Activity."

Houghten, R.A., et al., *Nature*, vol. 354, 8486 (1991), "Generation and Use of Synthetic Peptide Combinatorial Libraries for Basic Research and Drug Discovery."

Cwirla, S.E., et al., *Proc. Natl. Acad. Sci. USA*, vol. 87, 6378–6382 (1990), "Peptides on Phage: A Vast Library of Peptides for Identifying Ligands."

Fodor, S.P.A., et al., *Science*, vol. 251, 767–773 (1991), "Light–Directed, Spatially Addressable Parallel Chemical Synthesis."

METHOD OF CONDUCTING A PLURALITY OF REACTIONS

BACKGROUND OF THE INVENTION

The present invention lies in the field of methods and apparatus for preparing large arrays of polymers, receptors, and other compounds. More particularly, it lies in the fields of automated methods for preparing diverse arrays of polymers and of techniques for directing specified materials to predefined locations on a substrate.

Very diverse collections of compounds are often desired in research and other applications. Microtiter plates conventionally contain wells for testing as many as 96 different compounds. For many applications, 96 represents an unacceptably small number of samples. Further, when the compounds of interest are rare or valuable, the test samples must be minuscule. Unfortunately, signals from such small samples can be lost or diluted in the relatively large volume wells of a conventional microtiter plate. If the wells were made smaller and placed in higher densities on microtiter plates, suitable methods would still be needed for accurately delivering small aliquots to specified wells, and for identifying wells containing compounds that exhibit a desired activity.

Often the compounds of interest are polymers, such as nucleic acids, polysaccharides, or peptides. Some attempts have been made to synthesize a limited number of peptide sequences on, for example, a number of "rods." See, for example, Geysen, et al., *J. Immun. Meth.* (1987) 102:259–274, incorporated herein by reference for all purposes, which describes a procedure in which peptide syntheses are carried out in parallel on several rods or pins (to complement standard microtiter plates, 96 were used in the described method). The Geysen et al. method is limited in the number of sequences that can be synthesized in a reasonable amount of time. For example, Geysen et al. report in the above journal that it has taken approximately 3 years to synthesize 200,000 peptide sequences. In addition, such methods have continued to produce fewer peptide sequences for study than are often desired. Even if the large number of desired compounds could be produced quickly, they would not be readily accessible for further study. The 96 pin arrays of Geysen et al. would occupy far too much space to rapidly screen thousands of candidate polymers.

Techniques have recently been introduced for synthesizing large arrays of different peptides and other polymers on solid surfaces. For example, in Pirrung et al., PCT Publication No. WO 90/15070, incorporated herein by reference for all purposes, a technique is disclosed for generating arrays of peptides and other materials using, for example, light-directed, spatially-addressable synthesis techniques. See also, Fodor et al., PCT Publication No. WO 92/10092 (incorporated herein by reference for all purposes) which discloses, among other things, a method of gathering fluorescence intensity data, various photosensitive protecting groups, masking techniques, and automated techniques for performing light-directed, spatially-addressable synthesis techniques. Arrays containing up to 64,000 different elements have been formed using this technology. See, U.S. patent application Ser. No. 805,727, filed Dec. 6, 1991, which is incorporated herein by reference for all purposes. Because of their relationship to semiconductor fabrication techniques, these methods have come to be referred to as "Very Large Scale Immobilized Polymer Synthesis," or "VLSIPS™" technology. Such techniques have met with substantial success in, for example, screening various ligands, such as peptides, to determine their relative binding affinity to a receptor such as an antibody.

In some applications, it is desirable to study pre-formed collections of synthetic chemical compounds or natural product extracts. For example, it would be desirable to "immortalize" a collection of chemical samples from a rain forest threatened with destruction. In addition, thousands of different synthetic compounds often are cataloged in "libraries" of Universities and corporations. Unfortunately, the compounds of these libraries are not readily accessible for systematic study.

Methods for immobilizing collections of materials on a solid substrate are known. For example, U.S. Pat. No. 4,562,157 issued to Lowe et al., and incorporated herein by reference for all purposes, discusses a technique for attaching biochemical ligands to surfaces through a photochemically reactive arylazide. Irradiation of the azide creates a reactive nitrene moiety which reacts irreversibly with macromolecules in solution to form a covalent bond. The high reactivity of the nitrene intermediate, however, results in both low coupling efficiencies and many potentially unwanted reactions through nonspecific reactions.

An improved method for immobilizing collections of compounds is disclosed in Barrett et al., PCT Publication No. WO 91/07087 which is incorporated herein by reference for all purposes. This publication discloses a technique for immobilizing arrays of anti-ligands, such as antibodies or antigens, hormones or hormone receptors, oligonucleotides, polysaccharides, and other materials. Cycles of irradiation on different regions of a surface and immobilization of different anti-ligands allows formation of an immobilized matrix of anti-ligands at defined sites on the surface. The immobilized matrix of anti-ligands permits simultaneous screenings of a liquid sample for ligands having high affinities for certain anti-ligands of the matrix.

While the technique disclosed in PCT Publication No. WO 91/07087 as well as the VLSIPS™ technique are useful for preparing and using large arrays of materials, other techniques emphasizing efficient formation and use of much larger arrays of individual compounds would be desirable. If a very large group of compounds is used to form a diverse array, the number of individual locations on the array can be enormous. For example, to synthesize all dimer from 100 monomer starting materials requires 100,000 ($100^2$) separated locations. Forming an array of this size can be a daunting task. Further, once the array is produced, it can become quite difficult to locate specific members of the array for further processing or study.

Some work has been done to automate synthesis of polymer arrays. For instance, in Fodor et al., PCT Publication No. WO 92/10092, a method is described for using a computer-controlled system to direct a VLSIPS™ procedure. Further, Southern, PCT Application No. WO 89/10977 describes the use of a conventional pen plotter to deposit three different monomers at twelve distinct locations on a substrate. These monomers were subsequently reacted to form three different polymers, each twelve monomers in length. This reference also discusses the possibility of using an ink-jet printer to deposit monomers on a substrate. Wong et al., European Patent Application No. 260 965 describes a process in which a single polymer species in solution was putatively deposited in a single spot on a substrate by an apparatus resembling an ink-jet printer. However, neither the method described in the Wong et al. reference nor the method described in the Southern application concerns very large arrays of polymers. Further, the methods described in these two references would be unacceptably slow in accessing specific elements of a large array.

SUMMARY OF THE INVENTION

The present invention is directed to methods and apparatus for preparing large arrays of chemical compounds. It is also directed to methods for using such arrays in a variety of applications, such as screening compounds in drug development research. The chemical elements of the array are located on very small predefined zones or "cells" on a substrate surface. In one embodiment, a rotatable substrate surface is divided into tracks and/or sectors that allow identification of each cell's location. In another embodiment, a substrate surface is divided into cells that are automatically accessed from a few reference points by a dead reckoning navigation technique. Thus, reactants or other materials (e.g. from a library of compounds) are quickly and automatically delivered to any cell on the substrate surface by a dispenser. In many embodiments, the sequence of steps necessary to deliver specified reactants to certain groups of cells will be prerecorded and controlled by a processor such as a computer. The reactants will then be delivered to precise locations by, for example, micropipettes, electrophoretic pumps, or mechanisms adapted from ink-jet printing technology.

In one aspect of the present invention, the reactants are monomers and the cells of the array contain polymers having different monomer sequences. Thus, the present invention provides a method for synthesizing a large array of different polymers on a substrate. A first monomer solution is delivered to a first set of cells on a suitably derivatized substrate. Thereafter, a second monomer solution is delivered to a second set of cells, a third monomer solution is delivered to a third set, and so on until a number of cells each have one species of free monomer located therein. These monomers are then reacted with the surface, washed, and prepared for reaction with a new set of monomers. Dimers, trimers, and ultimately polymers of controlled length and monomer sequence are prepared by repeating the above steps with different groupings of the cells. In alternative embodiments, the polymers or other compounds of the array are delivered to the cells as complete species and, thus, the above polymer synthesis steps become unnecessary. Regardless of how the array is formed, the properties of its individual components can be studied by conducting simultaneous reactions in each cell. In this way a large number of reactions can be studied in parallel. In some cases, samples from one array may be accessed and moved to a second array where a reaction is conducted.

In one embodiment, the system for conducting reactions (such as polymer synthesis) on selected cells includes a substrate on which a plurality of cells are located and surrounded by non-wetting surface regions. Thus, the reactants in one cell will not flow to adjacent cells where they could contaminate the reaction. In preferred embodiments, the cells of the array are defined by selective irradiation of a substrate surface containing photolabile, hydrophobic protecting groups. In areas where the surface is irradiated, the hydrophobic protecting groups can be removed to define cells. When an aqueous or other polar reactant solution is deposited in the cell, it will have a relatively large wetting angle, thereby preventing flow to adjacent cells.

In some embodiments, the substrate includes digitally encoded instructions governing the sequence of deposition steps necessary to control the array of reactions. The instructions are typically readable by optical, electrical or magnetic sensors. Preferably, the cells and encoded instructions are located on tracks embedded on the disk surface. In this embodiment, a "read head" is necessary to receive the encoded information for further processing. In addition to the sequence of deposition steps, the encoded instructions will, in some embodiments, identify characteristics or properties of the polymers located in individual cells.

In preferred systems, the reactants are stored in one or more reservoirs which are available to a dispenser. The dispenser delivers the individual reactants from the reservoirs to the various cells on the disk surface. Typically, the dispenser will be mounted on an arm that can be moved across the substrate surface to any position by an actuator. The entire process is governed by a processor that controls the position of the dispenser with respect to the substrate and the reactant to be delivered. In this way, precise control over a very large array of cells and reactions is available.

A further understanding of the nature and advantages of the inventions herein may be realized by reference to the detailed description of the specification and the associated drawings.

DETAILED DESCRIPTION OF THE INVENTION AND PREFERRED EMBODIMENTS

Figure 1A:
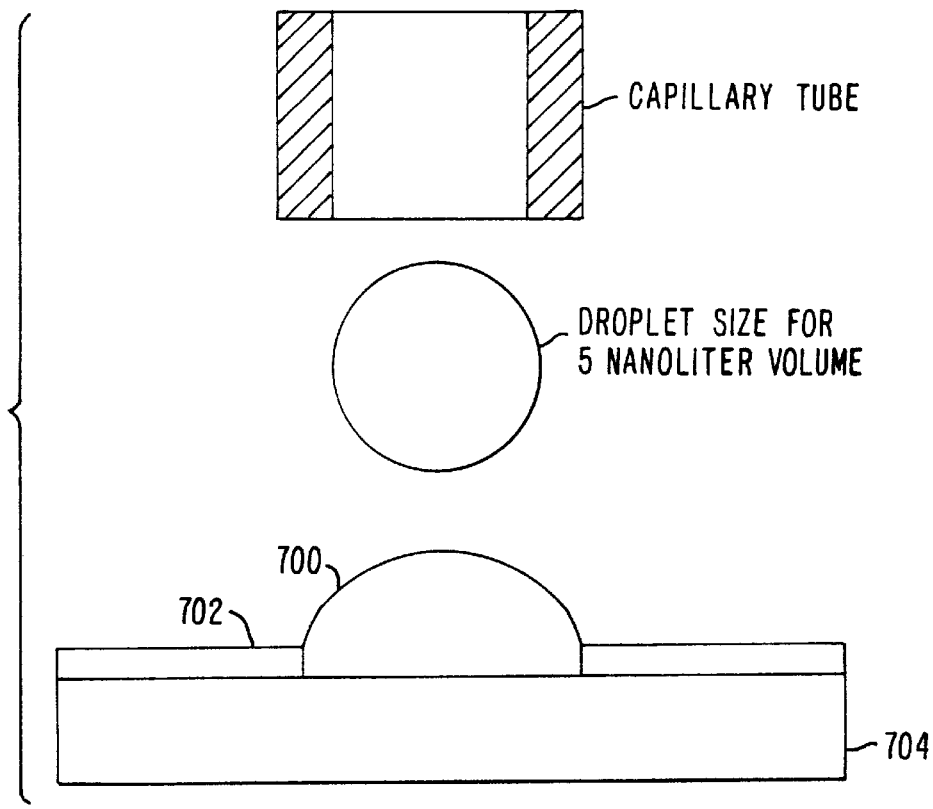
FIG. 1(A) displays a side view of a reactant solution in a cell surrounded by a hydrophobic mask according to one embodiment of the present invention.

| DETAILED DESCRIPTION OF THE INVENTION AND PREFERRED EMBODIMENTS | |
|---|---|
| I. | Glossary |
| II. | Overview of the Invention |
| III. | Isolation of Reaction Areas |
| | A. Dimples or recesses |
| | B. Controlling the Wetting Angle |
| IV. | Moving the Dispenser with Respect to the Substrate |
| | A. Mapping the Frame of Reference |
| | B. Rotational Mechanisms |
| V. | Delivering the Reactant Solution |
| VI. | Conducting the Reactions |
| VII. | Example |
| | A. Apparatus |
| | B. Locating Desired Cells |
| | C. Accessing Selected Cells |
| | D. Depositing Reactants in Selected Cells |
| | E. Peptide Synthesis |
| | F. Imaging the Array |
| VIII. | Conclusion |

I. Glossary

The following terms are intended to have the following general meanings as they are used herein:

1. Substrate: A material having a rigid or semi-rigid surface. In many embodiments, at least one surface of the substrate will be substantially flat, although in some embodiments it may be desirable to provide dimples, wells, raised regions, etched trenches, or the like. According to other embodiments, small beads or pellets may be provided on the surface within dimples or on other regions of the surface.

2. Cell: A cell is a localized area on a substrate which is to be used for conducting a reaction. This use of "cell" should not be confused with the common biological use of "cell." In some instances, the cells (reaction locales) of this invention will contain one or more biological cells for study. When the biological usage of "cell" is intended, it will be clearly indicated herein. Some reactions within a cell involve binding between a ligand and a receptor, and other reactions, for example, involve synthesis of a selected polymer. A cell may have any convenient shape, e.g., circular, rectangular, elliptical, wedge-shaped, etc. In some embodiments, cells are smaller than about 1 $cm^2$, more preferably less than 1 $mm^2$, still more preferably between about 100 $\mu m^2$ and 1 $mm^2$.

3. Substantially Pure: A polymer or other compound is considered to be "substantially pure" when it exhibits characteristics that distinguish it from the polymers or compounds in other cells. For example, purity can be measured in terms of the activity or concentration of the compound of interest. Preferably, the compound in a cell is sufficiently pure such that it is the predominant species in the cell. According to certain aspects of the invention, the compound is 5% pure, more preferably more than 10% pure, and most preferably more than 20% pure. According to more preferred aspects of the invention, the compound is greater than 80% pure, preferably more than 90% pure, and more preferably more than 95% pure, where purity for this purpose refers to the ratio of the number of compound molecules formed in a cell having a desired structure to the total number of non-solvent molecules in the cell.

4. Monomer: In general, a monomer is a member of a set of small molecules which are or can be joined together to form a polymer. The particular ordering of monomers within a polymer is referred to herein as the "sequence" of the polymer. As used herein, monomer refers to any member of a basis set used for synthesis of a polymer. For example, dimers of the 20 naturally occurring L-amino acids form a basis set of 400 monomers for synthesis of polypeptides. Different basis sets of monomers can be used at successive steps in the synthesis of a polymer. Furthermore, each of the sets may include protected members which are modified after synthesis. The invention described herein can readily be applied in the preparation of diverse types of polymers. Such polymers include, for example, both linear and cyclic polymers of nucleic acids, polysaccharides, phospholipids, and peptides having either α-, β-, or ω-amino acids, heteropolymers in which a known drug is covalently bound to any of the above, polyacetates, polyamides, polyarylene sulfides, polycarbamates, polycarbonates, polyesters, polyethyleneimines, polyimides, polynucleotides, polyphosphonates, polysiloxanes, polysulfones, polysulfoxides, polyureas, polyurethanes, or other polymers which will be apparent upon review of this disclosure.

5. Protective Group: A material which is bound to a monomer or other compound or group and which can be selectively removed therefrom to expose an active site such as, in the example of an amino acid, an amine group. A protective group will typically be used to block one reactive site of a bifunctional monomer from reacting during an addition reaction such as in the formation of a peptide from amino acids. A protective group can also cover certain regions of a substrate surface to impart certain properties such as non-wetability and to define cell perimeters or other features.

6. Head: A head is a device that reads, records, or erases signals stored on a suitable medium, such as magnetic or optical storage disks. The portion of the medium along which the head moves is called the "track." The head will typically be a transducer that senses (reads) or generates (writes) a signal corresponding to information provided by the medium or a processor. The transduction will typically involve electromagnetic fields or radiation, depending upon the type of media employed.

7. Receptor: Receptors used with the present invention may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A ligand is a molecule that is recognized by a particular receptor. Examples of ligands that can be investigated by this invention include, but are not restricted to, agonists and antagonists for cell membrane receptors, toxins and venoms, viral epitopes, hormones (e.g., opiates, steroids, etc.), hormones, peptides, enzymes, enzyme substrates, cofactors, drugs, lectins, sugars, oligonucleotides, nucleic acids, oligosaccharides, proteins, and antigens. A "Ligand Receptor Pair" is formed when two macromolecules have combined through molecular recognition to form a complex. Specific examples of receptors which can be investigated by this invention include, but are not restricted to the following:

a) Microorganism receptors: Determination of ligands which bind to receptors, such as specific transport proteins or enzymes essential to survival of microorganisms, is useful in developing new classes of antibiotics. Of particular value would be antibiotics against opportunistic fungi, protozoa, and those bacteria resistant to the antibiotics in current use.

b) Enzymes: For instance, the present invention can be used to identify ligands that bind to the binding site of enzymes such as the enzymes responsible for cleaving neurotransmitters, and ligands that bind to certain receptors to modulate the action of the enzymes which cleave the different neurotransmitters, as would be useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the development of vaccines of which the immunogen is based on one or more of such sequences or lead to the development of related diagnostic agents or compounds useful in therapeutic treatments such as for autoimmune diseases (e.g., by blocking the binding of the "self" antibodies).

d) Nucleic Acids: Sequences of nucleic acids may be synthesized to establish DNA or RNA binding sequences.

e) Catalytic Polypeptides: These receptors are polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant. Catalytic polypeptides and others are described in, for example, PCT Publication No. WO 90/05746, WO 90/05749, and WO 90/05785, which are incorporated herein by reference for all purposes.

f) Hormone receptors: Hormone receptors include, for example, the receptors for insulin and growth hormone. Determination of the ligands which bind with high affinity to a receptor is useful in the development of, for example, an oral replacement of the daily injections which diabetics must take to relieve the symptoms of diabetes, and in the other illustrative case, a replacement for the scarce human growth hormone which can only be obtained from cadavers or by recombinant DNA technology. Other examples include the vasoconstrictive hormone receptors; determination of those ligands which bind to these receptors may lead to the development of drugs to control blood pressure.

g) Opiate receptors: Determination of ligands which bind to the opiate receptors in the brain is useful in the development of less-addictive replacements for morphine and related drugs.

II. Overview

The present invention provides a method and apparatus for conducting a number of different reactions in parallel on a single substrate. It improves on certain prior methods (e.g. the method of Geysen et al. discussed above) by providing a greater density of reaction sites, a more rapid technique for conducting numerous reactions, and a more accessible collection of reaction sites. Because the reactions are conducted in parallel, the number of separate washing and other reaction steps can be minimized. Further, the reactions at different reaction sites can be controlled independently. Thus, the reactant concentrations and other parameters can, to some extent, be varied independently from reaction site to reaction site, thus optimizing the procedure. The invention can be used for a variety of purposes. For example, it can be used as a synthesis tool (as for example in peptide syntheses), as a screening tool (as for example in screening compound libraries for drug activity), or as a monitoring/diagnostic tool (as for example in medical or environmental testing).

As a tool for studying existing materials, the present invention can be employed to immobilize vast collections of synthetic chemical compounds or natural product extracts. In such methods, compounds are delivered by dispensing systems of the type described below to specified cells where they can be assayed for specific activities. As an example, a large complement of different human receptors could be deposited on a disk, one in each well. Then, a plant/animal extract could be screened for binding to different receptors. Competitive assays or other well-known techniques can be used to identify such activities.

In some embodiments, more than one cell of a disk will have the same compound immobilized therein. The reaction of that compound with various compounds such as the members of the chemical library of the type discussed above can be tested by dispensing small aliquots of each member of the library to a different cell. A "caged biotin" (described in Barrett et al., U.S. patent application Ser. No. 612,671, the PCT counterpart of which was previously incorporated herein by reference), or other immobilization technique can be used to immobilize the compounds to specific cells. Such techniques permit a variety of materials to be immobilized on the cells, including functional receptors, or biological cells bearing receptors. When the array contains the same or similar compounds in each cell, the immobilization procedure is simplified, because the coupling chemistry is consistent from cell to cell.

As a synthesis tool, the present invention can be used to prepare arrays of diverse polymers. This is accomplished by successively depositing monomers in groups of cells. For example, assume a monomer "A" is to be bound to the substrate in a first group of selected cells. If necessary, all or part of the total array of cells is activated for binding by flowing appropriate reagents over all or part of the substrate, or by depositing the appropriate reagents (with a dispenser as described below) in the selected cells for example. After the dispenser is filled with a reagent containing monomer A, the dispenser and/or the substrate are moved so that the dispenser can deposit a small quantity of monomer A in each of the first group of selected cells. The activated cells are in fluid contact with the dispensed material, thereby binding monomer A on the substrate directly or indirectly (via a linker) in the first selected cells.

Thereafter, the unreacted materials are removed from the substrate and a monomer "B" is coupled to a second group of selected cells, some or all of which may be included among the first selected cells. The second selected cells will be available to the dispenser through translation and rotation of the dispenser and/or the substrate. If necessary, a step is performed for activating at least the second group of cells. After monomer B is appropriately deposited, it is bound or reacted at the second selected cells. In this particular example, the resulting sequences bound to the substrate at this stage of the synthesis process can be, for example, A, B, and AB. The process is repeated, optionally with additional monomers, to form a vast array of sequences of desired length at known locations on the substrate.

Whether the present invention is used to synthesize a collection of polymers, immobilize one type of receptor, or immobilize a collection of compounds, the resulting array can be used for a variety of purposes, such as drug discovery and diagnostic assays. As described above, a collection of peptides or other bio-active compounds can be assayed for activity against one or more receptors. By quickly identifying materials having a strong affinity for the receptor of interest, researchers may discover potential new drugs. In other embodiments, the arrays produced by the present invention can be used to diagnose, measure, and/or monitor specific conditions in organisms. Specific binding patterns on premade arrays can be expected to accurately identify specific pathogens or other factors present in the sera of a patient. In still other embodiments, the present invention can be used to monitor the quality of pharmaceuticals or other materials, particularly biomolecules produced by, for example, fermentation processes. In such uses, very specific patterns or "fingerprints" on a very large array will correlate with the purity of the compound of interest. Subtle or not so subtle changes in the preparation containing the compound of interest will show up as variations in a baseline binding pattern of the array.

In the delivery systems of the present invention, a small, precisely metered amount of reactant solution is dispensed into each cell. This can be accomplished by a variety of delivery techniques. For example, conventional micropipetting apparati can be adapted to dispense 5 nanoliter or smaller droplets from a capillary. Such droplets can fit within a cell having a diameter of 300 $\mu$m or less when a non-wetting mask of the invention is employed. In another embodiment, the dispenser can be a piezoelectric pump that generates charged droplets that can be guided to the cell by an electric field as employed in conventional ink-jet printers.

The reactant solutions in the individual cells must often be prevented from moving to adjacent cells. This may be ensured by providing an appropriate barrier between the various cells of the substrate. For example, a hydrophobic material can be used to coat the region surrounding the individual cells. Such materials prevent aqueous (and certain other polar) solutions from moving to adjacent cells. Of course, when non-aqueous or nonpolar solvents are employed, different surface coatings will be required. By choosing appropriate materials (substrates, hydrophobic coatings, and reactant solvents), one can control the contact angle of the droplet with respect to the substrate surface. Large contact angles are desired because the area surrounding the cell remains unwetted by the solution within the cell. In one embodiment of the invention, the perimeters of the individual cells of an array formed on a hydrophilic substrate are defined by selectively irradiating a surface covered with photocleavable hydrophobic protective groups. In the irradiated areas, the protective groups are removed from the substrate to form lipophilic cells.

In some embodiments, the cells can be further defined by dimples in the substrate surface. This will be especially advantageous when a head or other sensing device must contact or glide along a substrate surface. The dimples can also act as identification marks directing the dispenser to the cell of interest.

The dispenser of the present invention can be aligned with respect to the appropriate cells by a variety of conventional systems. Such systems, which are widely used in the microelectronic device fabrication and testing arts, can deliver droplets to individual cells at rates at up to 3–10 drops per second. The translational (X-Y) accuracy of such systems is well within 1–5 $\mu$m. The position of the dispenser stage of such systems can be calibrated with respect to the position of the substrate by a variety of methods known in the art. For example, with only one or two reference points on the substrate surface, a "dead reckoning" method can be provided to locate each cell of the array. The reference marks in any such systems can be accurately identified by using capacitive, resistive or optical sensors. Alternatively, a "vision" system employing a camera can be employed.

In another embodiment of the present invention, the dispenser can be aligned with respect to the cell of interest by a system analogous to that employed in magnetic and optical storage media fields. For example, the cell in which the monomer is to be deposited is identified by its track and sector location on the disk. The dispenser is then moved to the appropriate track, while the disk substrate rotates. When the appropriate cell is positioned below the dispenser, a droplet of monomer solution is released.

III. Isolation of Reaction Areas

A. Dimples or recesses

If the substrates used in the present invention are to contain dimples or other recesses, the dimples must be sufficiently small to allow close packing on the substrate. Preferably, the dimples will be less than 1 mm in diameter, more preferably less than 500 $\mu$m in diameter, and most preferably less than 300 $\mu$m in diameter. The depth of such dimples will preferably be less than 100 $\mu$m and more preferably less than 25 $\mu$m below the upper surface of the substrate.

Dimples having these characteristics can be produced by a variety of techniques including laser, pressing, or etching techniques. For example, a suitable dimpled substrate surface can be provided by pressing the substrate with an imprinted "master" such as those commonly used to prepare compact optical disks. In addition, an anisotropic etching technique employing photolithography can be employed. In such techniques, a mask is used to define the cell regions of the substrate. After the substrate is irradiated through the mask, selected regions of the photoresist are removed to define the arrangement of cells on the substrate. The dimples may be cut into the substrate with standard plasma or wet etching techniques. If the substrate is a glass or silicon material, suitable wet etch materials can include hydrogen fluoride or other common wet etchants used in the field of semiconductor device fabrication. Suitable plasma etchants commonly used in the semiconductor device fabrication field can also be employed. Such plasma etchants include, for example, mixtures of halogen containing gases and inert gases. Typically, a plasma etch will produce dimples having a depth of less than 10 $\mu$m, although depths of up to 50 $\mu$m can be obtained under some conditions.

Another method for preparing a suitably dimpled surface employs photochemically etchable glass or polymer sheets. For example, a photochemically etchable glass known as "FOTOFORM" is available from Corning Glass Company (New York). Upon exposure to radiation through a mask, the glass become soluble in aqueous solutions. Thereafter, the exposed glass is simply washed with the appropriate solution to form the dimpled surface. With this material, well-defined dimples can be made having aspect ratios of 10 to 1 (depth to diameter) or greater and depths of up to 0.1 inches. Dimple diameters can be made as small as 25 $\mu$m in a 250 $\mu$m thick glass layer.

B. Controlling the Wetting Angle

Even when a dimpled surface is employed, it is often important to ensure that the substrate material is not wetted beyond the cell parameters. To ensure that the solutions in the individual cells do not wet the surrounding surface and contaminate other cells, various techniques can be applied to control the physical interactions that affect wetting. Whether or not a liquid droplet will wet a solid surface is governed by three tensions: the surface tension at the liquid-air interface, the interfacial tension at the solid-liquid interface and the surface tension at the solid-air interface. If the sum of the liquid-air and liquid-solid tensions is greater than the solid-air tension, the liquid drop will form a bead (a phenomenon known as "lensing"). If, on the other hand, the sum of the liquid-air and liquid-solid tensions is less than the solid-air tension, the drop will not be confined to a given location, but will instead spread over the surface. Even if the surface tensions are such that the drop will not spread over the surface, the contact or wetting angle (i.e., the angle between the edge of the drop and the solid substrate) may be sufficiently small that the drop will cover a relatively large area (possibly extending beyond the confines of a cell). Further, small wetting angles can lead to formation of a thin (approximately 10 to 20 Å) "precursor film" which spreads away from the liquid bead. Larger wetting angles provide "taller" beads that take up less surface area on the substrate and do not form precursor films. Specifically, if the wetting angle is greater than about 90°, a precursor film will not form.

The contact angle is determined by the same three parameters that determine whether a liquid will spread. Specifically, the contact angle is given by the following expression, known as Young's equation:

$$\cos \theta = (\sigma_{sa} - \sigma_{s1})/\sigma_{1a}$$

where $\theta$ is the wetting angle, $\sigma_{sa}$ is the solid-air tension, $\sigma_{s1}$ is the solid-liquid tension, and $\sigma_{1a}$ is the liquid-air surface tension.

The surface tensions that determine the wetting properties of a liquid-solid interface are governed by thermodynamic considerations including the chemical constituents of the liquid and the solid substrate. The liquid-air surface tension for various chemicals is easily measured by a variety of techniques such as those described in Adamson, *Physical Chemistry of Surfaces* (John Wiley and Sons, 5th Ed. (1990)), which is incorporated herein by reference for all purposes. The solid-air tension is not determined so easily. Nevertheless, the difference of the solid-liquid and solid-air tensions can, for a given system, be determined empirically from a Zisman plot. In this approach, the contact angles are measured for a homologous series of liquids on a given solid surface. For some liquid in the series, a "critical contact angle" is observed, beyond which lower surface tension liquids wet the surface. The liquid-air surface tension of the liquid at this critical contact angle is assumed to be the surface tension of the solid. This approach has been found to provide quite reasonable results for low energy solids such as Teflon, polyethylene, hydrocarbons, etc. The information gained from such studies can be used to optimize substrate compositions to increase wetting angles for a given reactant solution in the array.

The surface chemistry can be varied from position to position on the substrate to control the surface free energy and, hence, the contact angle of the reactant solution drops. In this way, an array of cells can be defined on the substrate surface. For example, if an aqueous reactant solution is used, the region inside the cells can be hydrophilic, while the region surrounding the cells can be hydrophobic. Methods for controlling the local surface free energy of a substrate include a variety of techniques that will be apparent to those skilled in the art.

In one method, various protecting groups are used to control the chemical composition of the surface. For example, a mono-layer of hydrophobic photoprotecting groups can be coupled to, for example, linker molecules attached to the substrate surface. The surface is then selectively irradiated (or otherwise activated) through a mask to expose those regions where the cells are to be located. This cleaves the protecting groups from the substrate surface, causing the cell regions to be less hydrophobic than the surrounding area. Because hydrophobic materials have lower surface free energies (surface tensions) than water, the solution droplet in the cell beads rather than spreads. Suitable hydrophobic protecting groups for use with the present invention include, but are not limited to, the alkyl silanes (e.g., octadecyl silane).

For some systems, other protecting groups will be preferable. For instance, if a non-aqueous solution chemistry is employed, the protecting groups can be tailored to increase the wetting angle for the particular solution being used. Further, if different solvents are to be contacted with the same cell during polymer synthesis, the protecting groups surrounding that cell can be changed during the course of the process by a VLSIPS™ technique. This will ensure that no matter what type of solution is added to the cell, a large wetting angle is obtained.

Figure 1B:
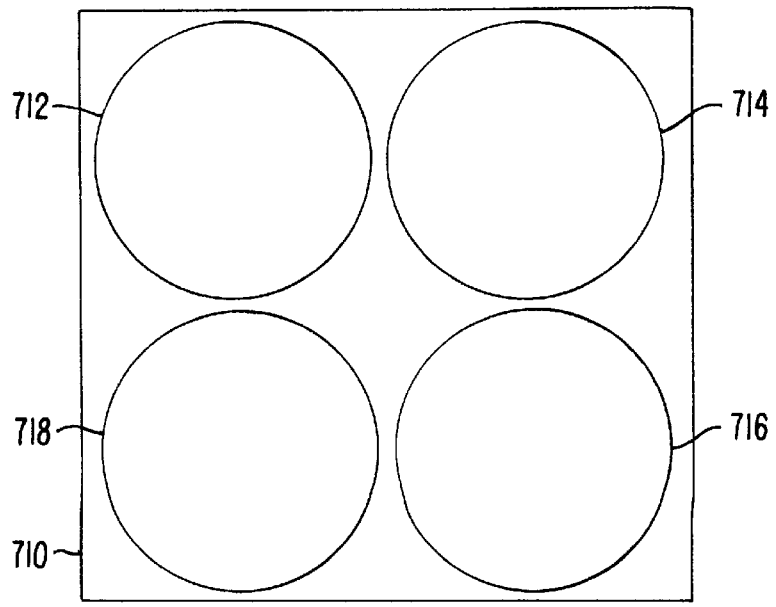
FIG. 1(B) displays a top view of an array of cells having circular perimeters.

FIG. 1A shows a droplet 700 after it was deposited by a micropipette on a non-wetting mask 702 above a substrate 704 according to the present invention. The aspect ratio shown (dome height equals one-half the width) was empirically determined to be stable using a non-wetting mask having a two millimeter by two millimeter square area (the cell diameter was 0.2835 millimeter). FIG. 1B illustrates a top view of a high-density droplet array 710. The four cells of the array are shown at 712, 714, 716 and 718. Because the cell array is defined with photolithographic techniques and the hydrophobic mask is on the order of one monolayer thick, the droplets can be packed very closely together.

IV. Moving The Dispenser With Respect To The Substrate

A. Mapping the Frame of Reference

To consistently deposit reactant droplets at precisely specified locations, a common frame of reference between the delivery instrument and the substrate is required. In other words, the reference coordinates of the instrument must be accurately mapped onto the reference coordinates of the substrate. Ideally, only two reference points on the substrate are required to completely map the array of cells. The dispenser instrument can locate these reference points and then adjust its internal reference coordinates to provide the necessary mapping. Of course, in this situation, the dispenser instrument must provide precisely repeatable movements. Further, the individual cells must not move with respect to the reference marks on the substrate after the reference marks have been formed. Unfortunately, pressing or other mechanical operations commonly encountered during fabrication and use of a substrate can warp the substrate such that the correspondence between the reference marks and the cells is altered.

To allow for this possibility, a substrate containing both "global" and "local" reference marks can be employed. Only two global reference marks are needed to define the initial frame of reference. From these marks, the dispenser instrument can determine where each cell of the originally imprinted substrate is located. In an initial, "course" adjustment, the dispenser is positioned in the local area of the cell of interest. Once in the local region, the dispensing instrument looks for local reference marks to define a local frame of reference. From these, the dispenser is accurately positioned over the cell of interest. In this manner, the effects of warpage or other deformation can be minimized. The number of local reference marks is determined by the amount of deformation expected in the substrate. If the substrate is sufficiently rigid that little or no deformation will occur, very few local reference marks will be required. If substantial deformation is expected, however, more local reference marks will be required.

Starting at a single reference point, the micropipette or other dispenser can be translated to other cells of the substrate by a correct distance in the correct direction (as noted above, this is the "dead reckoning" navigational technique). Thus, the dispenser can move from cell to cell, dispensing correctly metered amounts of reactant. In order to initially locate the reference point and align the dispenser directly over it, a vision or blind system can be employed. In a vision system, a camera is rigidly mounted to the dispenser nozzle. When the camera locates the reference point(s), the dispenser is known to be a fixed distance and direction away from the point, and a frame of reference is established. Blind systems locate the reference point(s) by capacitive, resistive, or optical techniques, for example. In one example of an optical technique, a laser beam is transmitted through or reflected from the substrate. When the beam encounters a reference mark, a change in light intensity is detected by a sensor. Capacitive and resistive techniques can be applied similarly. A sensor registers a change in capacitance or resistivity when a reference point is encountered.

For purposes of this invention, the spacing between the individual cells preferably will be on the order of 10 μm or less. Further, the angular relation between the cells is preferably consistent, to within 0.1 degrees. Of course, the photolithographic or other process used to define the arrangement of cells will accurately define the angle and spacing. However, in subsequent processes (e.g., pressing processes), the angle can be distorted. Thus, in some embodiments, it may be necessary to employ "local" reference points throughout the array.

Translational mechanisms capable of moving with the desired precision are preferably equipped with position feedback mechanisms (encoders) of the type used in devices for semiconductor device manufacturing and testing. Such mechanisms will preferably be closed loop systems with insignificant backlash and hysteresis. In preferred embodiments, the translation mechanism will have a high resolution, i.e. greater than five motor ticks per encoder count. Further, the electromechanical mechanism will preferably have a high repeatability relative to the cell diameter travel distance (preferably ±1–5 μm).

To accurately deposit a drop of reactant solution on the substrate, the dispenser nozzle must be placed a correct distance above the surface. For a drop having a volume of approximately five nanoliters, the dispenser tip preferably will be located about 5–50 μm above the substrate surface when the drop is released. More preferably, the drop will be about 10 μm above the substrate surface when the drop is released. The degree of control necessary to achieve such accuracy can be attained with a repeatable high-resolution translation mechanism of the type described above. In one embodiment, the height above the substrate is determined by moving the dispenser toward the substrate in small increments, until the dispenser tip touches the substrate. At this point, the dispenser is moved away from the surface a fixed number of increments which corresponds to a specific distance. From there, the drop is released to the cell below. Preferably, the increments in which the dispenser moves will be less than about 5 μm and more preferably less than about 2 μm.

In an alternative embodiment, the dispenser nozzle is encircled by a sheath that rigidly extends a fixed distance beyond the dispenser tip. Preferably, this distance corresponds to the distance at which the solution drop will be most easily delivered to the cell. Thus, when the sheath contacts the substrate surface, the movement of the dispenser is halted and the drop is released. It is not necessary in this embodiment to move the dispenser back, away from the substrate, after contact is made. In this embodiment, as well as the previous embodiment, the point of contact with the surface can be determined by a variety of techniques such as by monitoring the capacitance or resistance between the tip of the dispenser (or sheath) and the substrate below. A rapid change in either of these properties is observed upon contact with the surface.

B. Rotational Mechanisms

In some embodiments, the substrate rotates on an axis and the dispenser moves radially on a line from the substrate axis to the substrate perimeter. These embodiments employ mechanisms analogous to those encountered in the computing and recording arts. In magnetic media, a rigid or floppy disk contains magnetized and unmagnetized regions that correspond to bits of data. In some instances, the direction of magnetization corresponds to the bits of data. The magnetization of these bits can be changed by moving a "recording head" close to the bit. The recording head generates magnetic flux that will either magnetize, demagnetize, or leave unchanged a selected region on the disk. Thus, by carefully controlling both the magnetic flux on a write head and the relative position of the magnetic disk with respect to the write head, data can be recorded at preselected locations on the disk surface. Further, by using standard formats for subdividing and labelling the disk, recorded data can be rapidly located and retrieved by a "read head."

Two widely used types of magnetic disk are the floppy disk typically made from a mylar film and the hard disk typically made from a rigid material such as an aluminum disk. Both disks require very close correspondence between the read/write head and the recording media (i.e. the disk). In a floppy disk, the read and write head actually touches a magnetic disk, and must be lubricated to avoid excessive wear. In contrast, a hard disk read/write head never touches the surface, but rather "flys" at submicron distances above the hard disk surface on a hydrodynamic bearing surface. The hydrodynamic bearing is created by the rapid rotation of the disk (typically, about 3600 rpm) and overcomes the force of gravity, thus preventing the head from "crashing" onto the disk. In this way, disk wear is minimized and the head can be rapidly moved across the disk surface.

Large disk memories employ a stack of hard disks coated on both sides with the magnetic material and rotating together on a common spindle. A set of read/write heads is used: two are required for each plate. Typically, large disk memory will have an access time of about 20 milliseconds.

In optical media, a beam of laser light is used to either read from or write to a disk. When the read laser beam is passed over the surface of the disk, it normally encounters the flat unrecorded regions of the surface and is reflected back in the direction from which it originated. A sensor of a form well-known in the art monitors the reflected light to detect recorded information on the disk surface. Most prerecorded optical disks (commonly known as "compact disks") have a series of very small pits cut into the disk surface. Typically, the pit size can be as small as about 1 μm. When the laser beam passes over a pit, the path length of the reflected beam increases. At the edge of the pit, the beam will be divided into portions having different path lengths which can destructively interfere with one another. This change in intensity is interpreted as recorded information that can be interpreted by appropriate processing circuitry. Preferably, the pit depth will be one quarter of the wavelength of the read laser light. Thus, the total change in path length of a laser beam passing over a pit will be one half wavelength, a distance corresponding with the maximum possible destructive interference.

Information can be recorded on an optical disk by using a laser beam to change the optical properties of the disk surface. For example, the laser beam can ablate small regions of the surface to create pits. Other means of recording information include, heating regions of the substrate above the Curie point and, thereafter, changing the magnetization of the region, and heating regions of the substrate to create readable bumps such as described in Marchant, *Optical Recording*, Addison-Wesley (1990), incorporated herein by reference in its entirety for all purposes. Other methods of optical recording suitable for use with the present invention will be known to those of skill in the art.

Figure 2A:
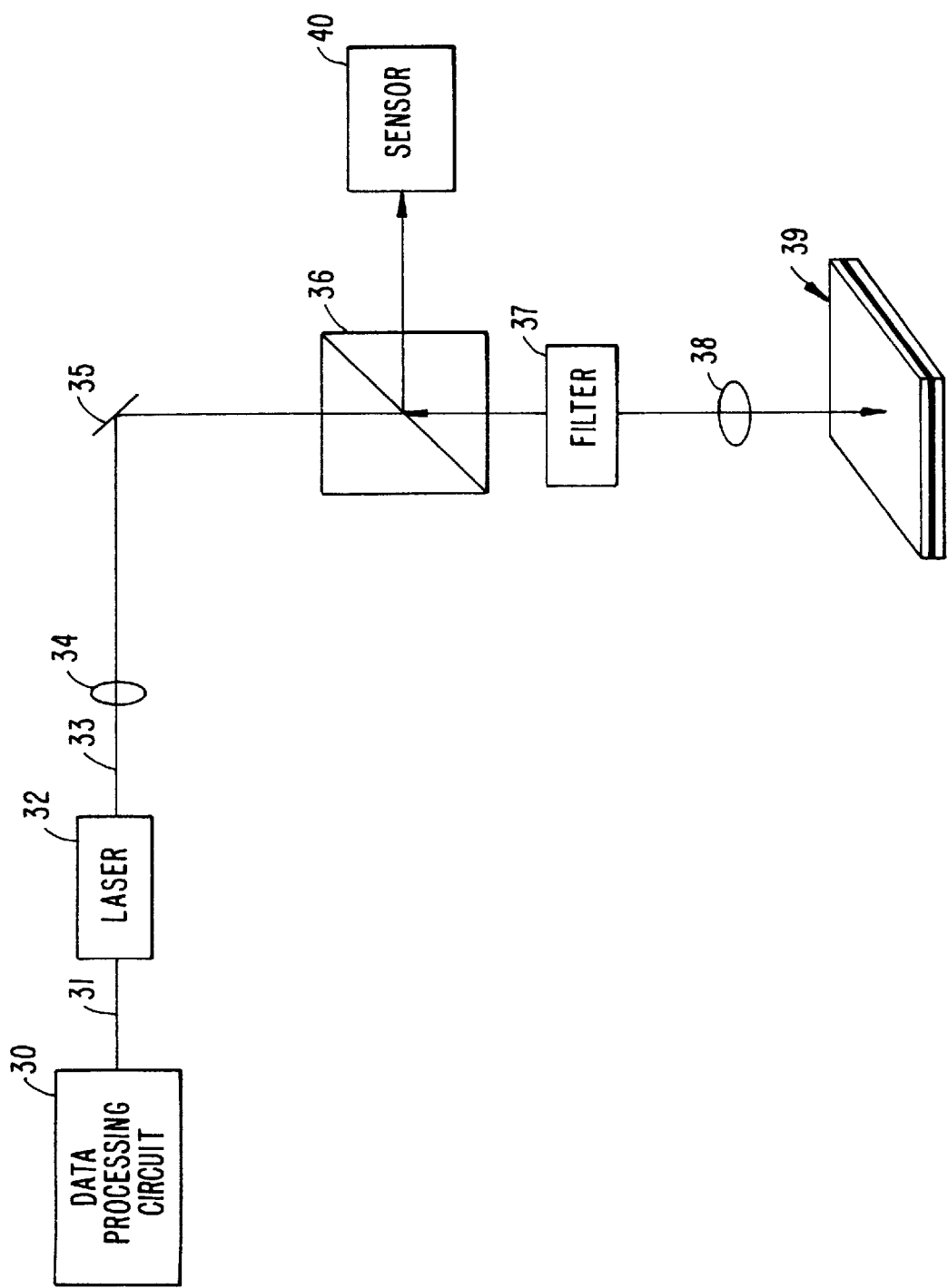
FIGS. 2A–2B display elements of an optical record/read apparatus and bump-forming media that can be used with such apparatus.

FIG. 2A illustrates one example of an electro-optical system for recording data on a data storage medium in accordance with various embodiments of the present invention. The recording system includes a digital data processing circuit 30 whose output on line 31 controls the pulsed variable-intensity laser 32. The laser beam 33 emerging from the laser 32 is collimated by a lens 34 and then reflected by a mirror 35. The reflected beam from the mirror is propagated through a beam splitter 36.

The laser beam emerging from the beam splitter 36 is passed through a filter 37, which can be a quarter-wavelength plate, and then propagated through an objective lens 38 which focuses the laser beam on the moving optical data storage medium 39. Light reflected back from the medium 39 is collected by the lens 38 and propagated through the filter 39 to the beam splitter 36, which propagates the reflected light to a light sensor 40.

Figure 2B:
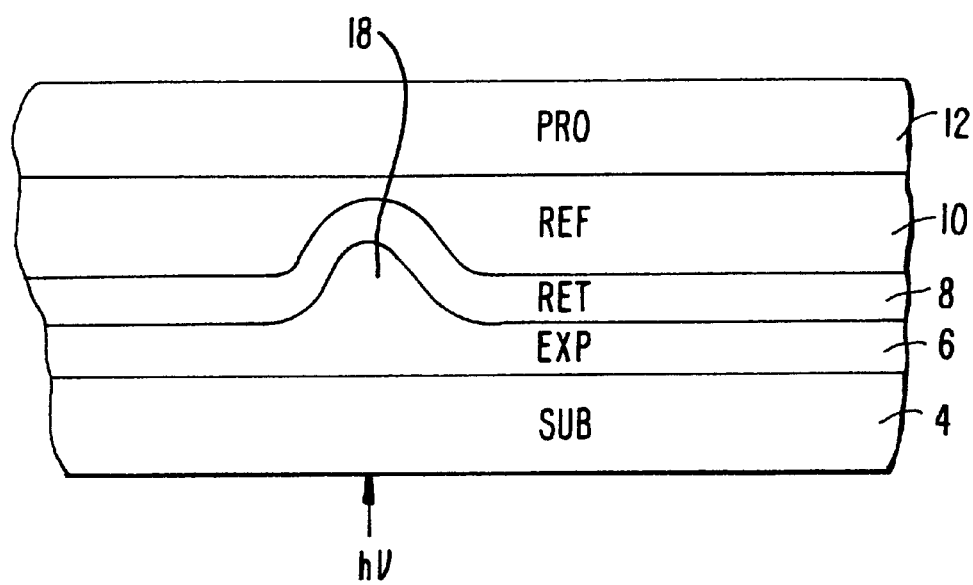

The laser 32 is preferably a high-power laser (2–15 mW at the media surface) and is either continuous or pulsed. The wavelength of the laser beam 33 is the "write" or "record" wavelength, and is either continuous, shaped, or pulsed. The write beam typically enters the medium at the substrate side, as shown in FIG. 2B, and passes through a transparent substrate 4 into an expansion layer 6. The expansion layer, which is absorptive of light at the laser wavelength, rises in temperature due to the absorption, but is kept from localized expansion by the rigid substrate 4 and a retention layer 8 (which is in its glassy state). Expansion pressure thus builds up and the retention layer begins to deform in a broad manner. Meanwhile, the temperature of the retention layer rises by conduction from the expansion layer, and possibly by light absorption as well. As the temperature of the retention layer increases, it approaches the glass transition temperature and a small weak area is formed around the axis of the incident beam. The expansion layer then flows into this weak area allowing expansion to be localized, thereby creating a well-defined bulge or bump 18. The retention layer 8 deforms accordingly to follow the contour of the bulge, and protrude into a soft reflective layer 10. When the laser is turned off, the various layers cool. The reflective layer 10 acts as a heat sink rapidly drawing heat away from the retention layer 8, and the retention layer 8 cools down below its glass transition temperature, increasing its shear modulus to lock in the deformation while the expansion layer 6 is still in its expanded state.

Erasure is achieved by using a laser beam of a different wavelength, one which is absorbed primarily by the retention layer 8. The expansion layer 6 may also be absorptive at this wavelength, to some degree, provided that the resulting temperature increase in the expansion layer is not great enough to record a mark. Absorption of the light from this beam by the retention layer will raise it to its rubbery state, at which point elastic forces in the expansion layer as well as the viscoelastic properties in the retention layer will draw the retention layer back to a bump-free configuration. Reflective layer 10 will naturally flow back into the void left by the retention layer.

In both magnetic and optical storage media, information must be quickly accessed. As mentioned, a diskette typically spins at about 300 RPM and a hard disk typically spins at about 3600 RPM. The actuator that moves the recording/reading head across the disk radius is also fast: for a diskette, it takes an average of about one-sixth of a second to move to any radial position on the disk, and for a hard disk, it takes only about 1/25th of a second.

In computer operating systems such as DOS, particular data such as program applications (e.g. spreadsheets, databases, etc.) and data files are stored as binary magnetic information at various locations on the surface of the disk. This information is organized on a series of concentric circles or "tracks." Hard disks have hundreds of such tracks, each of which is identified by a number, starting with track zero at the outer edge of the disk. Each track is divided into various "sectors" containing a predefined number of bytes. Like the tracks, the sectors are also numbered, starting with one (sector zero is reserved for identification rather than data storage). Thus, any particular piece of data can be located by defining the sector (or at least the first sector if the data file is large) on which it is recorded. By analogy to the above discussion on frames of reference, the tracks and sectors can be viewed as local reference marks.

On DOS formatted storage disks, the locations of the recorded data files are stored on a small "system area" of the disk. Specifically, the list of sectors on which a given data file resides is recorded in the system area of a DOS formatted storage disk. Thus, by inputting a file name, the system area of the disk can identify the location of the file on the magnetic disk. Steps can then be taken to move the read/write head to that location to access the file.

Like conventional data storage disks, the disks used to hold the compound arrays of the present invention can provide "system" information (i.e., tracking/location information) prerecorded on a blank disk. However, unlike conventional storage disks, the disks of the present invention also have "cells" in which the individual compounds of the matrix are synthesized or stored. These cells can be interspersed among the information tracks (including both system and data regions) in a variety of formats, as will be explained in the example below. The cells can take the form of dimples on the disk, especially if information is stored on magnetic media. However, other forms of cells can be used if the individual solution drops can be adequately isolated from each other. Using these and similar disk designs, the user can record and quickly access the location and cells by techniques well-known in the art.

Alternatively, the monomer (or other compound) solutions can be distributed from a closely packed array of capillaries, or from a slit-shaped container covered with a conductive screen having holes small enough to preclude leakage due to gravity alone. In these embodiments, the individual dispensers will have a limited range of movement over the disk radius and may even be fixed in space. In any of the above apparati, electrodes can be provided in the individual nozzles to provide electrical contact to the monomer solutions.

Figure 3A:
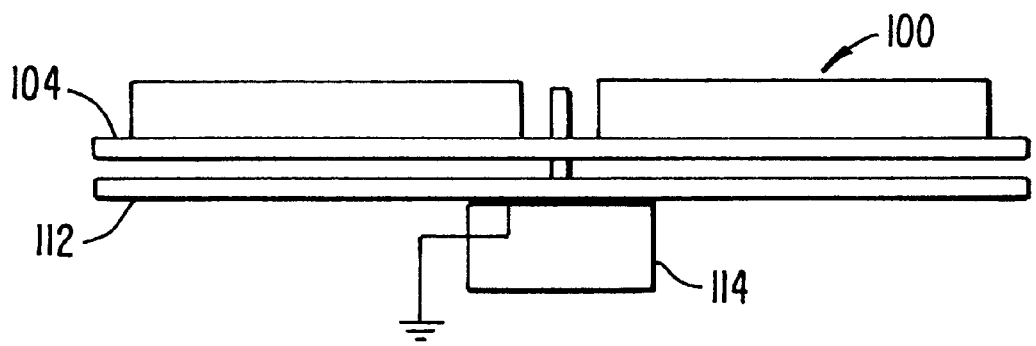
FIGS. 3A–3D display features of a dispensing apparatus for delivering several different reactants to a disk substrate.
Figure 3B:
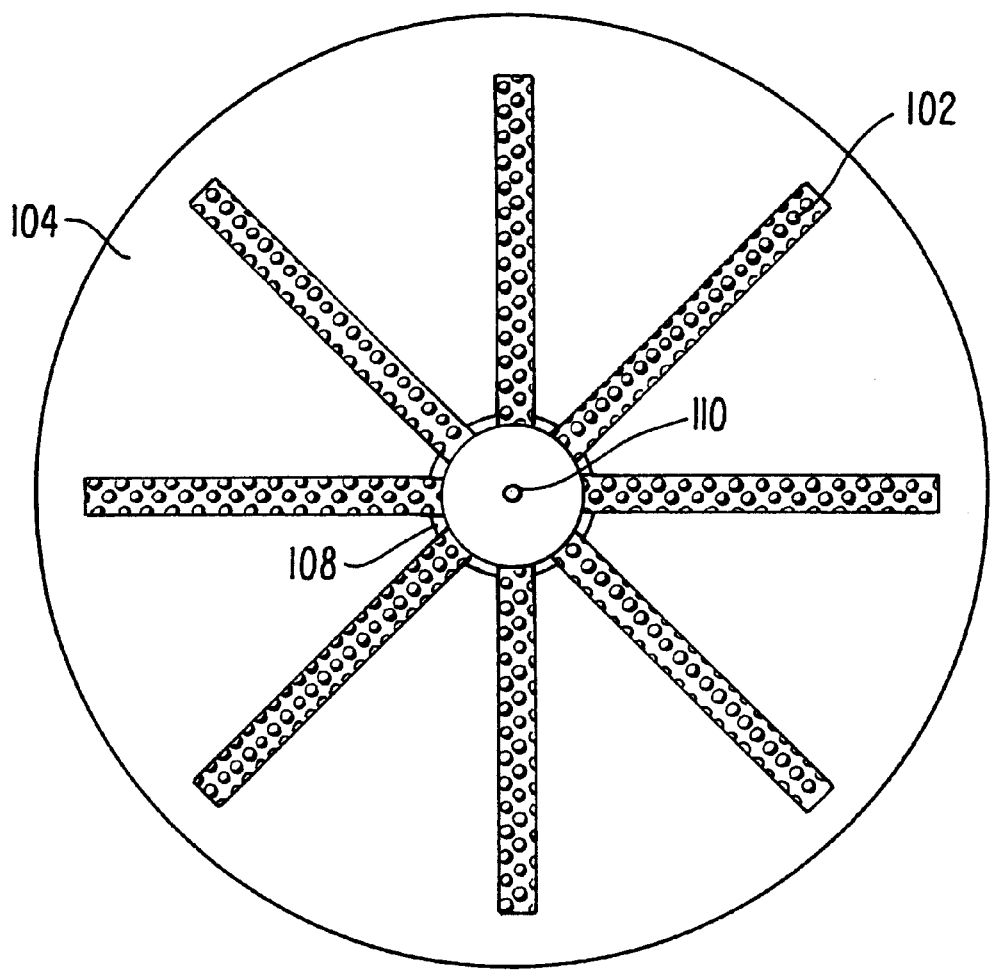
Figure 3C:
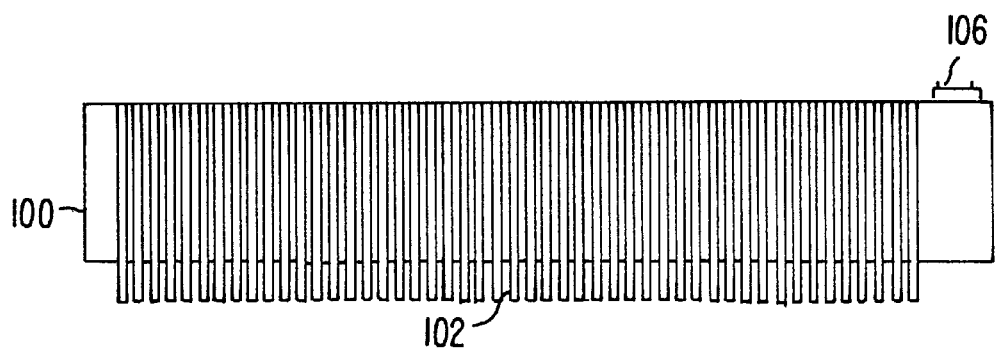
Figure 3D:
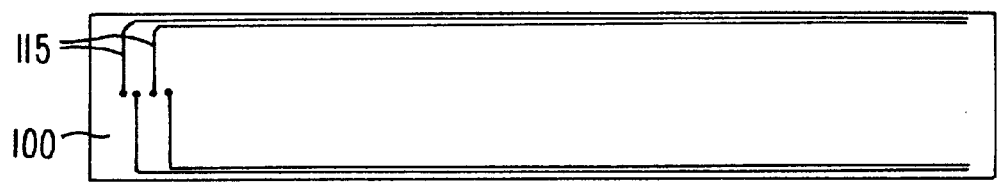

A preferred precision placement dispenser is shown in FIGS. 3A–3D. FIG. 3C is a side view of cartridge 100 which contains several capillaries 102 filled with various monomers. Electrodes (not shown) run down the center of each capillary 102. FIG. 3D is a top view of cartridge 100, showing an arrangement of leads 115 to the electrodes. The cartridges are loaded into a delivery plate 104 such that terminals 106 on the cartridge ends mate with terminals 108 on a spindle 110 as shown in top view FIG. 3B. Thus, a central power supply can control all the electrodes. The delivery plate 104 rotates above the substrate 112 as shown in FIG. 3A. Substrate 112 will, in many embodiments, be made from a conductive material held at ground, or a non-insulating material covering a plate held at ground. A servo motor 114 rotates the delivery plate 104 and the power supply selectively charges the electrodes so that drops of desired monomer will cross from the dispenser to the desired cells on substrate 112. If the basis set of monomers is sufficiently small, the capillaries may be held in fixed positions, relying on rotation of the substrate and electric fields to guide the charged droplets to the cells.

V. Delivering the Reactant Solution

As explained above, commercially available micropipettes are a preferred delivery mechanism for the present invention. Commercially available micropipettes, such as the A203XVY Nanoliter injector, are able to reproducibly dispense 4.6 nanoliter droplets. In some embodiments, the micropipette is accurately and precisely positioned above the cell, as described above, before the reactant solution is deposited.

In a different preferred embodiment, the reactant solutions will be delivered from a reservoir to the substrate by an electrophoretic pump. In such a device, a thin capillary connects a reservoir of the reactant with the nozzle of the dispenser. At both ends of the capillary, electrodes are present to provide a potential difference. As is known in the art, the speed at which a chemical species travels in a potential gradient of an electrophoretic medium is governed by a variety of physical properties, including the charge density, size, and shape of the species being transported, as well as the physical and chemical properties of the transport medium itself. Under the proper conditions of potential gradient, capillary dimensions, and transport medium rheology, a hydrodynamic flow will be set up within the capillary. Thus, bulk fluid containing the reactant of interest can be pumped from a reservoir to the substrate. By adjusting the appropriate position of the substrate with respect to the electrophoretic pump nozzle, the reactant solution can be precisely delivered to predefined cells.

In one particularly useful embodiment, the electrophoretic pump can be used to produce an array containing various fractions of an unknown reactant solution. For example, an extract from a biological material, such as a leaf or cell culture, might contain various unknown materials, including receptors, ligands, alkaloids, nucleic acids, and even biological cells, some of which may have a desired activity. If a reservoir of such extract is pumped electrophoretically, the various species contained therein will move through the capillary at different rates. Of course, the various components being pumped should have some charge so that they can be separated. If the substrate is moved with respect to the dispenser while the extract components are being separated electrophoretically, an array containing various independent species will be produced. This array can then be tested for activity in a binding assay or other appropriate test. Those elements of the array that show promising activity will be correlated with a fraction of the extract which can be isolated from another source for further study. In some embodiments, the components in the extract solution can be tagged with, for example, a fluorescent label. Then, during the process of delivering the solution with the electrophoretic pump, a fluorescence detector can determine when labeled species are being deposited on the substrate. In some embodiments, the tag will selectively bind to certain types of compounds within the extract, and impart a charge to those compounds.

In other embodiments, the present invention employs a solution depositing apparatus that resembles devices commonly employed in the ink-jet printing field. In fact, some ink-jet printers can be used with minor modification by simply substituting a monomer containing solution for ink. As mentioned, Wong, et al., European Patent Application 260 965, incorporated herein by reference for all purposes, describes the use of a commercial printer to apply an antibody to a solid matrix. In the process, a solution containing the antibody is forced through a small bore nozzle that is vibrating in a manner that fragments the solution into discrete droplets. The droplets are subsequently charged by passing through an electric field and then deflected onto the matrix material.

A conventional ink drop printer includes a reservoir in which ink is held under pressure. The ink reservoir feeds a pipe which is connected to a nozzle. An electromechanical transducer is employed to vibrate the nozzle at some suitable high frequency. The actual structure of the nozzle may have a number of different constructions, including a drawn glass tube which is vibrated by an external transducer, or a metal tube vibrated by an external transducer (e.g. a piezoelectric crystal) or a magnetostrictive metal tube which is magnetostrictively vibrated. Accordingly, the ink is ejected from the nozzle in a stream which shortly thereafter breaks into individual drops. An electrode may be present near the nozzle to impart a charge to the droplets.

Because these drops are to be charged and thereafter deflected by electrical signals, it is desirable to make these drops be as uniform in size as possible. It is also desirable to form these drops with a close spacing, because closer spacings result in better resolution. Also, it is desirable to form the drops into a small size so that the amplitude of the signals required to deflect these drops should not be excessive.

Figure 4:
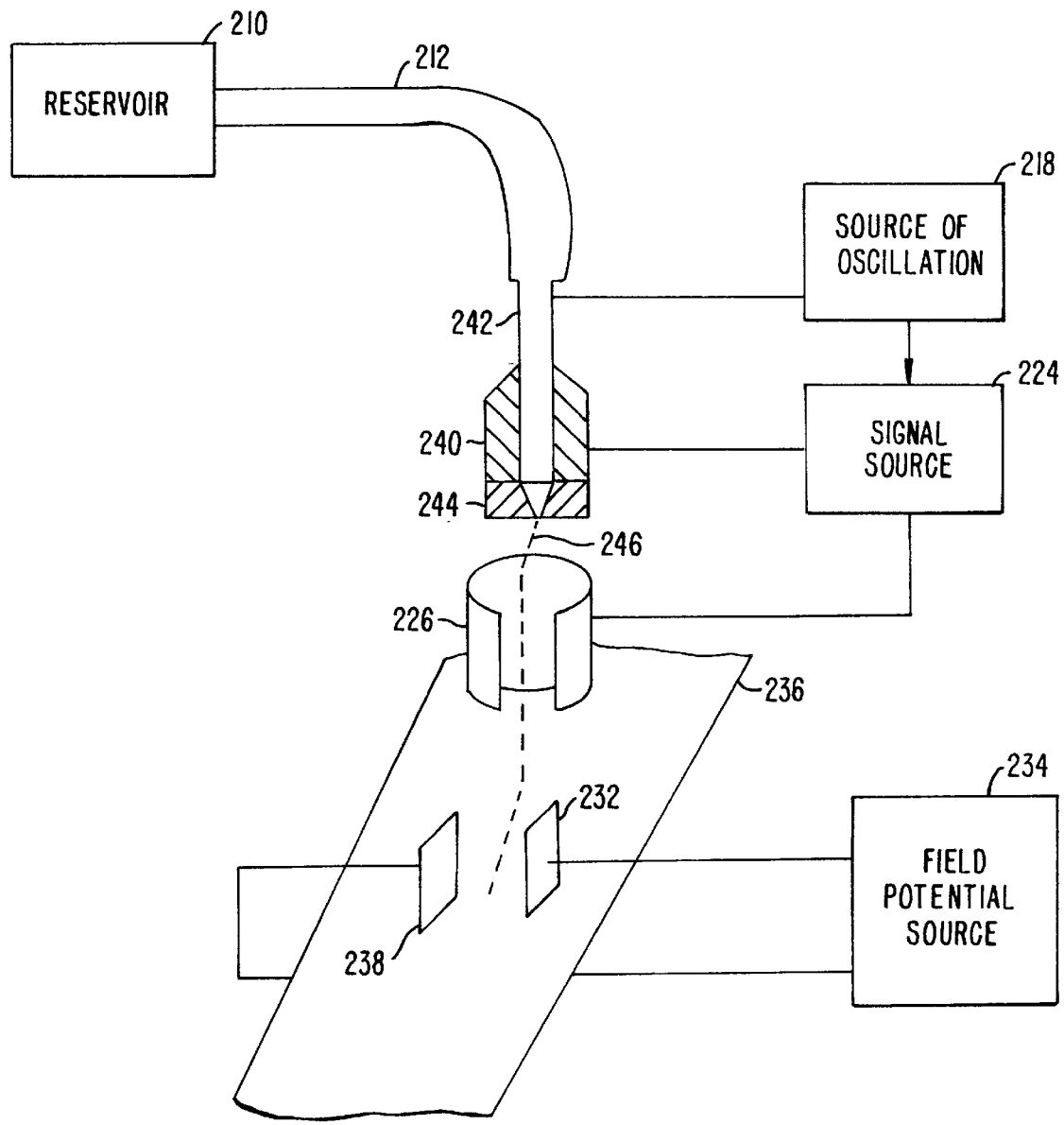
FIG. 4 displays elements of a typical guided droplet dispenser that can be used to deposit the reactant solutions of the present invention.

A schematic drawing of an ink drop dispenser (such as is described in U.S. Pat. Nos. 3,281,860 and 4,121,222, which are incorporated by reference herein for all purposes) which can be employed in the present invention is shown in FIG. 4. This apparatus comprises a reservoir 210 which contains a solution under pressure. Tubing 212 is connected to the reservoir 210 and terminates in a metal nozzle 242. Nozzle 242 is disposed within a hole provided in piezoelectric crystal 240. The end of the metal tube and of the piezoelectric crystal are made to coincide. The tubing and the piezoelectric crystal are soldered together to form a permanent waterproof attachment. The coincident ends of the crystal and the tubing are covered with a washer 244 which is termed an orifice washer. This washer has an opening 246 drilled therethrough through which the solution is emitted under pressure. A source of oscillations 218 is connected between the outside of the metal tubing 242 and the outside of the piezoelectric crystal 240. The construction is such that hermetic sealing can be employed which protects against electrochemical and atmospheric attack of the components.

The piezoelectric crystal 240 is vibrated substantially at the frequency of the source of oscillations causing the tubing and nozzle to vibrate whereby the solution stream breaks down into droplets 246. A signal source 224 which is synchronized by the source of oscillations is connected between the nozzle and the charging cylinder 226. As a result, each of the drops, which should be substantially the same mass, receives a charge, the amplitude of which is determined by the amplitude of the signal applied from the source 224 and the charging cylinder 226.

The charged drops, after passing through the charging cylinder, pass into an electric field which is established between two plates respectively 230 and 232 which are connected to a field potential source 234. As a result of the action between the field and the charge of each drop, the drops are deflected from their center line path between the plates in accordance with the charge which they carry. Thus, when they fall on an optionally moving writing medium 236, a deposition pattern occurs on the writing medium representative of the information in the signals.

Other suitable delivery means include osmotic pumps and cell (biological) sorters. An osmotic pump will deliver a steady flow of solution for a relatively long period. The construction of such pumps is well-known in the art, generally incorporating a solution of the extract of interest within a solvent permeable bag. Osmotic pressure is applied to the extract solution by solvent molecules diffusing across the bag to equalize a concentration difference. The extract is thus forced out of a nozzle in the bag at a constant rate. Cell sorters are also well-known in the art, and can be used in applications wherein it is desirable to apply single biological cells to distinct locations on the substrate.

Although the above embodiments have been directed to systems employing liquid droplets, minuscule aliquots of each test substance can also be delivered to the cell as miniature pellets. Such pellets can be formed from the compound of interest (e.g. ligands for use in an affinity assay) and one or more kinds of inert binding material. The composition of such binders and methods for the preparation of the "pellets" will be apparent to those of skill in the art. Such "mini-pellets" will be compatible with a wide variety of test substances, stable for long periods of time, suitable for easy withdrawal from the storage vessel and dispensing (i.e., non-tacky, preferably suspendable in a liquid such as physiological buffer), and inert with respect to the binding activity of receptors.

VI. Conducting the Reactions

Methods for synthesizing desired polymer sequences such as peptide sequences are well known to those of skill in the art. For example, the so-called "Merrifield" solid-phase peptide synthesis has been in common use for several years and is described in Merrifield, *J. Am. Chem. Soc.* (1963) 8:2149–2154 and Atherton, Solid Phase Peptide Synthesis, IRL Press, Oxford (1989), incorporated herein by reference for all purposes. Methods of synthesizing oligonucleotides are found in, for example, *Oligonucleotide Synthesis: A Practical Approach*, Gait, ed., IRL Press, Oxford (1984), incorporated herein by reference in its entirety for all purposes.

The preferred processes involve steps of first binding a "protected" monomer to a solid substrate such as glass, polymer or other non-swellable, insoluble, and otherwise reaction-compatible materials. By immobilizing the growing polymer, one simplifies subsequent purification procedures to washing steps, rather than the complicated recrystallization steps traditionally used. The monomers are protected by attaching chemical groups on a reactive terminus of the monomer so that the immobilized monomer—which has another reactive terminus coupled to the substrate—cannot further react with other dissolved monomers to form dimers. Merrifield originally used carbobenzoxy groups to protect the amine terminus of amino acid monomers from further reaction. After the first monomer was immobilized and washed free of dissolved monomer species, the carbobenzoxy groups were cleaved from the monomer by a mixture of hydrogen bromide in glacial acetic acid. Of course, other protective groups and cleavage mixtures can be used for particular monomers as is well-known in the art. For example, tert-butyloxycarbonyl-protected amino groups, cleavable with trifluoroacetic acid treatment can also be used in peptide synthesis. Additional $\alpha$-amino protecting groups include acyl type protecting groups (e.g., formyl, trifluoroacetyl, acetyl), aromatic urethane type protecting groups (e.g., benzyloxycarboyl (Cbz) and substituted Cbz), aliphatic urethane protecting groups (e.g., isopropyloxycarbonyl, cyclohexyloxycarbonyl) and alkyl type protecting groups (e.g., benzyl, triphenylmethyl).

Alternatively, the protecting groups on individual monomers can be photocleavable. Various suitable photoprotecting groups are disclosed in, for example, Fodor, et al., published PCT Application No. WO92/10092. In this embodiment, the entire substrate or selected cells can be exposed to radiation for activation. This approach is especially advantageous when the disk information is provided in an optically readable format. The read/write head in such a system can be used to direct light radiation to selectively activate various cells by deprotecting the monomers therein.

After the first monomer in a polymer sequence has been deprotected, a solution of the second monomer (with one reactive terminus protected) may be reacted with the immobilized first monomer. One well-known coupling reaction employs N,N'-dicyclohexylcarbodiimide in dimethylformamide solvent. Other coupling methods can be employed depending upon monomers used, as is well-known in the art. Subsequent washing, deprotection, and reaction steps will generate a polymer of the desired sequence. The polymer, in an array of many different polymers, can then be used in, for example, screening assays. Alternatively, individual polymers can be cleaved from the substrate and used elsewhere.

It may, of course, be necessary to "wash" certain cells of the array to remove reactant solutions between synthesis cycles. Such steps can be accomplished by removing the disk from the synthesizer and immersing it in a cleaning or other solution. Alternatively, the disk can be left on the platter in the synthesizer and a stream of fluid passed over it to clean off unreacted species. In other embodiments, a high pressure injector is used to "randomly access" cells and to wash off residues or left over solutions. In still other embodiments, a charged plate is lowered over the substrate surface to draw off the solutions. This is particularly advantageous when the reactant droplets were deposited by a process in which they were charged, as by a corona discharge or an electrophoretic pump. Because some residual charge will remain on the droplets when they are present in the cells, a charged plate of polarity opposite to that of the drops will draw them off of the substrate. This approach allows the substrate to be cleaned without removing it from the compartment in which the reactions take place.

Evaporation should be minimized, especially if the reagents used have low vapor pressures and the substrate or dispenser is spinning at sufficiently high rates of speed to cause convection at the surface of liquid drops. If the drops are sufficiently small, evaporation can cause the reactant concentration to increase and ultimately cause precipitation. The effects of evaporation can be minimized by sealing selected regions of the disk when they need not be accessible. Alternatively, the partial pressure of volatile reagents can be controlled to equalize the liquid and vapor phase fugacities so that there is a reduced thermodynamic driving force for evaporation. The partial pressure of the reagents may be increased by providing a relatively large reservoir of volatile reagents in a sealed chamber. Alternatively, solvents having a low vapor pressure under the conditions of interest can be used. In some cases, evaporation can be further controlled by application of a low vapor-pressure film or coverplate having a reverse cell pattern. Other methods of preventing evaporation are well-known in the physical chemical arts and may be used in the present invention.

VII. Example

A. Apparatus

This example and the following discussion are directed to the polymer synthesis embodiments of the present invention. This is not meant to suggest that the invention is to be used solely for synthesizing arrays of polymers. As described above, the methods and apparatus of the present invention can be applied with equal utility to other chemical and biological systems. For instance, in preparing and screening arrays of existing compounds, one can use methods and instruments similar to those discussed below for making and screening new compounds. Moreover, the following example is directed to a rotating disk substrate in which reference information is encoded on the disk. As explained above, other methods, such as those employing rectangular substrates with global and local reference marks, can be employed. Rectangular or spherical navigational coordinates can also be used.

Figure 5:
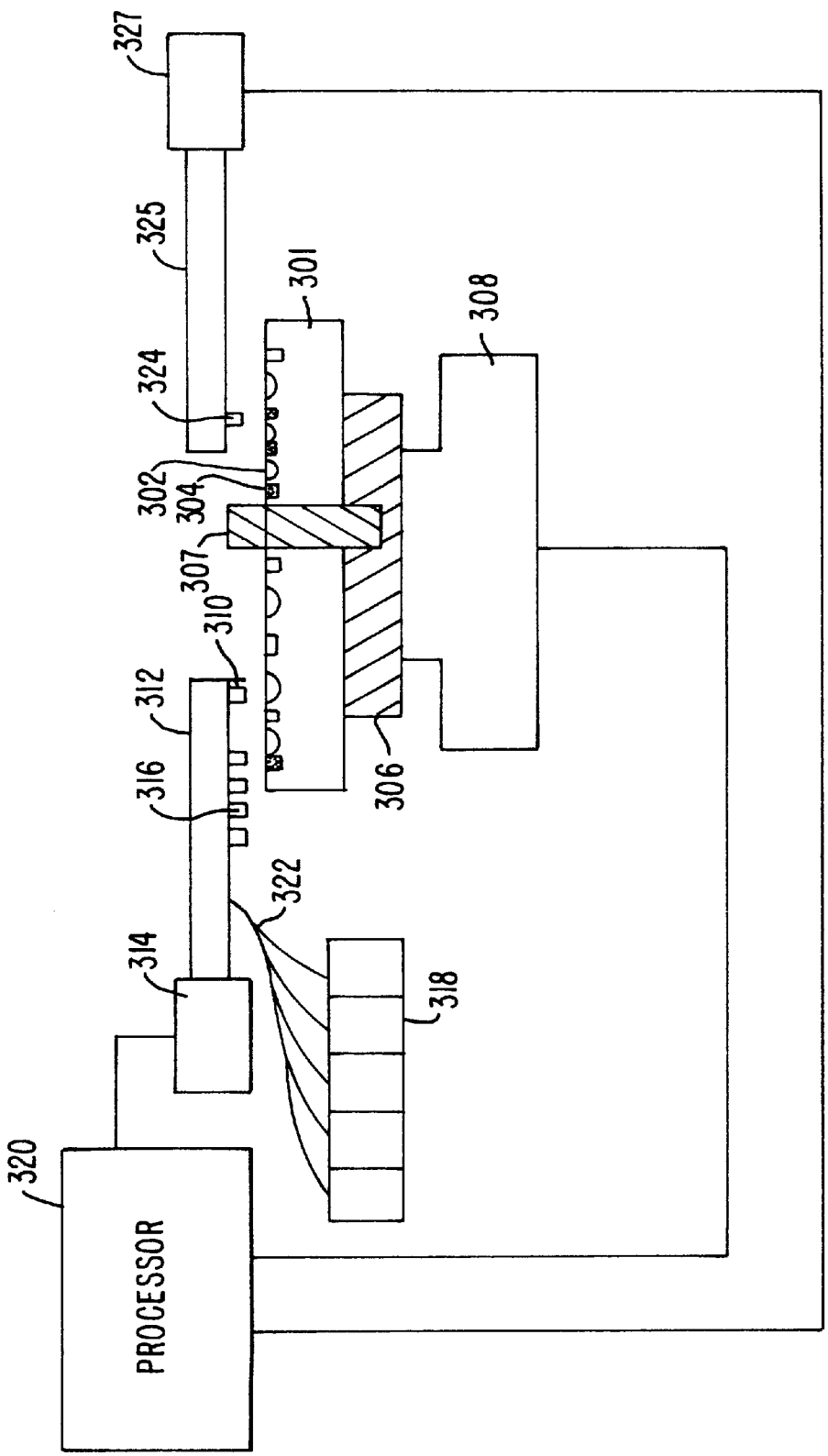
FIG. 5 displays a preferred embodiment of the present invention.

FIG. 5 illustrates an example of the invention in which various monomers are to be bound at selected cells of the substrate. The substrate may be biological, nonbiological, organic, inorganic, or a combination of any of these, existing as gels, sheets, tubing, containers, capillaries, pads, slices, films, plates, slides, etc. It is preferably flat, but may take on a variety of alternative surface configurations. For example, the substrate may contain raised or depressed regions on which the synthesis takes place.

In this embodiment, the substrate contains a magnetic or optical storage media coating on its surface at defined regions where digital information is stored. Of course, the entire substrate can be made from such storage media, so long as the material is compatible with the desired polymer synthesis. If a magnetic storage media is employed, the read/write head typically rides directly on or near the surface of the substrate. Thus, the cells are preferably located such that the polymers and oligomers are not rubbed away by the contact between the substrate and the recording head. One way to accomplish this is by providing dimples on the substrate surface to serve as cells. Thus, as the magnetic head rides over the surface, it does not shear off the polymers in the cells. If information is encoded on an optical storage media, the read/write head does not contact the surface, and dimpled cells are therefore optional.

Referring now to the synthesizer shown in FIG. 5, a disk substrate 301 includes a number of cell tracks 302 and encoded information tracks 304. The actual polymers of the array are synthesized in the individual cells on the cell tracks. The disk is mounted on a spindle 307 and a platter 306 which is rotated by a motor 308 at variable speeds. The individual monomer solutions are provided to the cells as droplets from dispenser 310. As explained above in connection with ink drop dispensers, the droplets can be charged by an electrode or conductive device inside the dispenser or dispenser nozzle. An attachment to the dispenser head can provide variable direction electric fields to guide the charged droplets to the appropriate cells. The dispenser itself can be a piezoelectric pump or other device capable of producing fine droplets of controllable size and spacing, as discussed above in connection with the ink drop dispenser. Alternatively, the droplets can be provided as neutral drops from a standard micropipette.

The dispenser is located at the end of an arm 312 capable of having its radial position controlled by an actuator 314 such as a voice coil actuator or other translation control device commonly used in the optical or magnetic disk storage technologies. In addition, the dispenser can have a plurality of capillary nozzles 316 for delivering individual monomer solutions. These nozzles can be movable along a track (not shown) on arm 312 or can be fixed on the arm, relying on translation by actuator 314 to reach the proper radial position.

The various monomer solutions are supplied from reservoirs 318 to the dispenser and nozzles through lines 322. The reservoirs can be pressurized to ensure adequate delivery rates of the monomer solutions to the dispenser. Typically, a control valve is used to ensure that the monomers are dispensed only when required. Other feed systems can also be used. For example, if reservoirs 318 are disposed above the dispenser, a gravity feed system can be used to ensure adequate delivery rates. In some embodiments, electric fields between the disk 301 and the dispenser 310 are used to "pull" the droplets of monomer solution out of capillary nozzles 316.

The pertinent commands directing the radial translation of arm 312, the rotation of disk 301, and the dispensing of appropriate monomer solutions are controlled by processor 320. Processor 320 can be a computer or workstation, such as an IBM PC or compatible system, an Apple MacIntosh, a Sun Microsystems SPARC station, or any other conventional system. In addition, it can be a dedicated microprocessor or hardware logic designed specifically to control the operation of the synthesizer. Processor 320 can also obtain data from and/or store data in internal or external storage devices such as RAM or cache memories, hard disk drives, CD ROMs, or other well known memory devices. Alternatively, data can be obtained from or written to disk 301 through read/write head 324. In one embodiment, head 324 senses information stored on information tracks 304, converts that information to electrical signals which are then interpreted by processor 320. Read/write head 324 utilizes standard principles used in magnetic and optical recording heads, as outlined above. The position of head 324 is controlled by an actuator 327 which controls the radial position of arm 325.

Although dispenser 310 and read/write head 324 are shown opposite one another in FIG. 5, it is desirable in some embodiments to mount them on the same arm or on arms proximate to one another. This is especially advantageous when the information governing the deposition in certain cell tracks 302 is recorded on information tracks 304 adjacent to the cell tracks where deposition is to take place. The information in tracks 304 can be slightly ahead of the "phase" of the cells in cell tracks 302, as will be described below.

In defining a protocol for rapid delivery to a variety of sectors, it is advantageous to deposit one monomer solution on certain cell tracks in succession. For example, when the first set of monomers is being deposited, monomer A is deposited in every cell of track 3, sector 7, or at least some fraction of the cells in sector 7. Of course, to obtain a maximally diverse array, this approach cannot be used at every stage of the deposition process, but it does help build some local redundancy into the system. The local redundancy in the polymer sequences has other advantages as explained below.

B. Locating Desired Cells

Two preferred types of information processing can be used in the practice of the present invention. The first relates to procedures for depositing the specific monomers at specific locations on the disk. This includes instructions directing the movement of the dispensers and the disk during deposition so that the desired array of polymers is synthesized. Thus, for instance, when the first monomers of the polymer are being deposited, instructions are provided to deposit alanine at track x, sectors 3, 4, and 6, track y, sectors 1, 2, and 3, track z, sectors 2, 4, 7, and 8, etc. In many instances, it will also be necessary to specify specific cells within the sector.

The second type of information processing relates to the monomer sequence listing, or identity, of the polymer associated with each cell. Related information such as the physical properties (polarity, degree of branching, etc.) and the binding constants for certain ligands can also be recorded for each cell, as well as other pertinent information useful and apparent to those of skill in the art. Preferably, the information is digitally encoded and presented in a format that can be read and written by conventional magnetic or optical heads. Desired characteristics of such heads have been described above.

The information can be recorded and stored in various locations. For example, completely prerecorded disks can be used. These will have both major types of information (the deposition protocol and the monomer sequence listing associated with each cell) recorded on a "blank" disk (i.e., a disk on which no monomers have yet been deposited). The synthesizer reads the deposition protocol from the disk and directs the monomer dispensers to the correct cells at correct time, ultimately synthesizing the desired array of polymers. The blank disk also has a listing of the monomer sequence for each cell so that cells of interest can be quickly identified. Alternatively, the blank disks can have only one type of information recorded. For instance, the deposition protocol can be stored elsewhere in the synthesizer, such as in a mass storage device, RAM, or a cache memory. Thus, the blank disk does not have to be read to determine the deposition protocol, allowing additional flexibility in specifying what polymers are to be synthesized. Contemporaneously with the deposition and polymer synthesis, the sequence listing in each cell can be written on the disk. In this way, the finished disk has a complete listing of the deposited polymer sequences and their locations.

Of course, it is also possible that the disk contains no monomer sequence listing or deposition protocol information. This information can be stored elsewhere in the synthesizer or archived on removable storage media. However, it will typically be preferable to keep at least the sequence listing information on the completed disk to reduce the risk of losing the information.

If information is to be recorded on the disk, it can be stored at any of several possible locations. On optical disks, the bit size is on the order of 1 $\mu$m, whereas the preferred cell size is about 100 $\mu$m. Thus, the pertinent information can be stored on thin tracks readable by the read/write head, while the cells can be located on larger tracks ("cell tracks"), parallel with the information tracks. The two types of tracks can form concentric circles (as in optical and magnetic disks), or they can form continuous spirals (as is possible in optical disks).

Referring to FIG. 6, various arrangements of information on the disk are provided. Information tracks are denoted as dotted lines, while the cell tracks are denoted by a series of circles. For example, when the information and cell tracks are concentric circles, all the information tracks can be located together near the inner perimeter of the disk as shown in FIG. 6A or near the outer perimeter of the disk as shown in FIG. 6B. Also, the information and cell tracks can alternate across the radius of the disk as shown in FIG. 6C. If no information is provided on the disk, the disk can appear as shown in FIG. 4D.

Figure 6A:
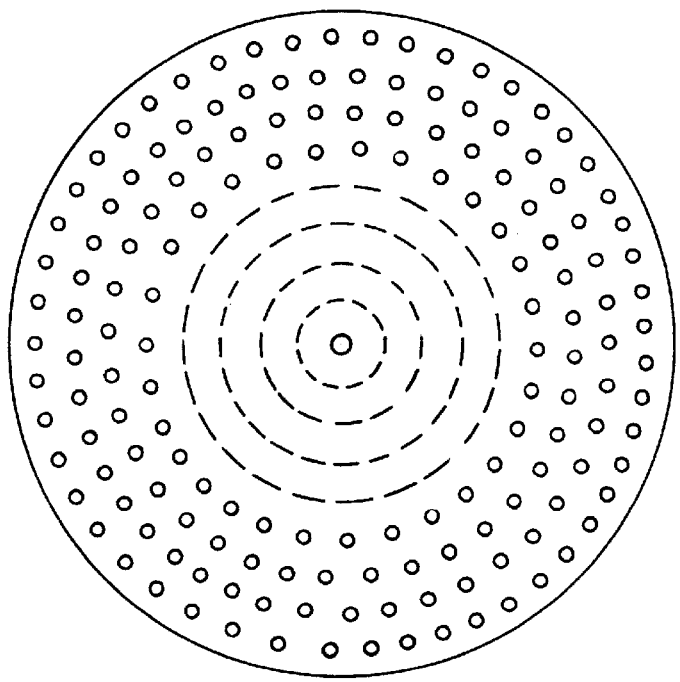
FIGS. 6A–6E show various formats for the disk arrays that can be used in certain embodiments of the present invention.
Figure 6B:
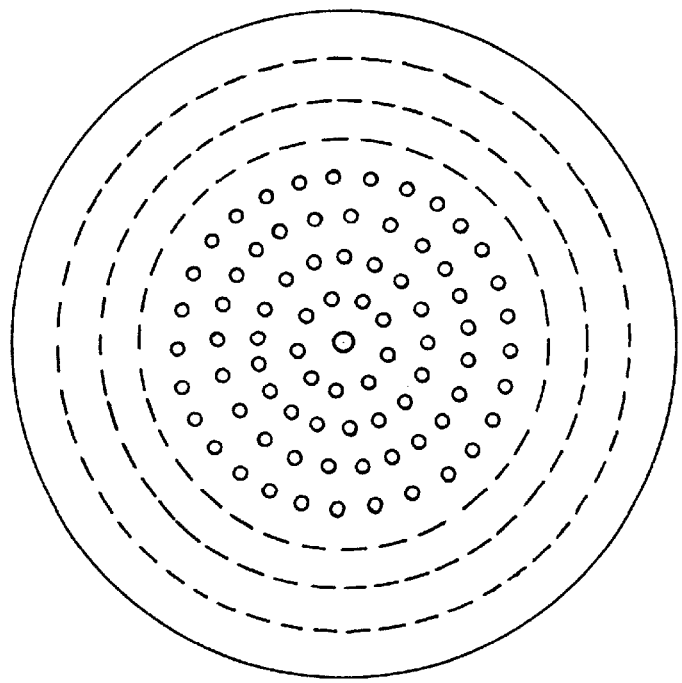
Figure 6C:
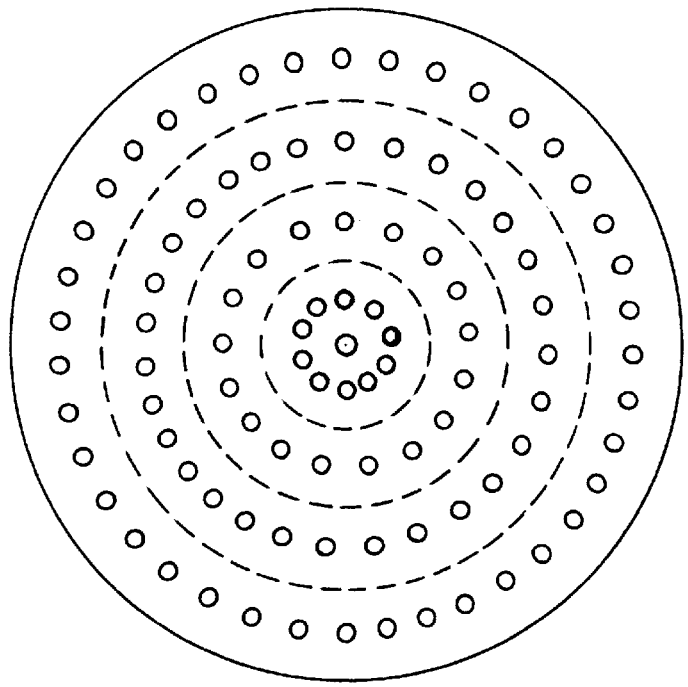
Figure 6D:
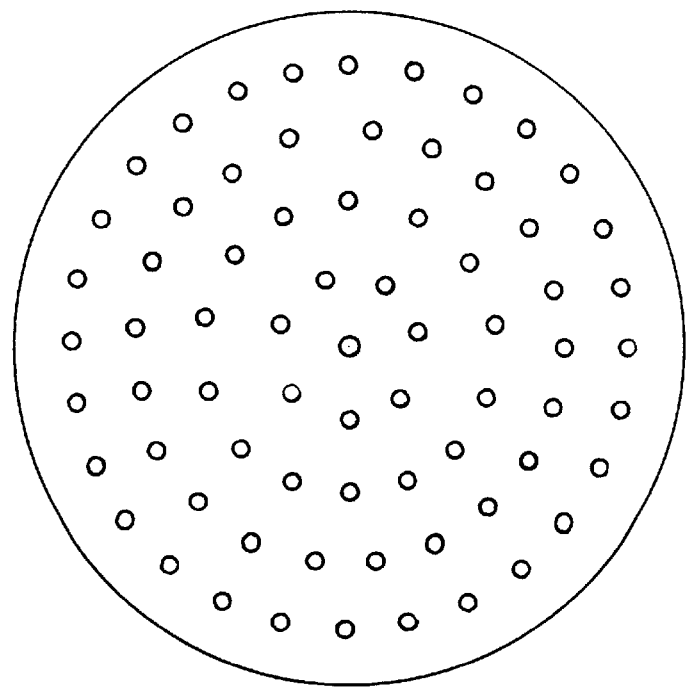

The information provided in these arrangements can be used in a variety of manners. For instance, if the alternating track format of FIG. 6C is employed, the read/write head can move to a first information track, read the deposition protocol for the first cell track, thereafter move to the first cell track, and deposit appropriate monomers in the cells as prescribed by the first information track. Thus, a first layer of monomers can be deposited by moving the dispensers and read write head radially across the surface of the disk. These first monomers can then be reacted, and the process repeated for the second layer of monomers. After a sufficient number of these track-by-track read and deposition cycles are completed, the polymer array is completed. During this process, the sequence listing information for each cell can also be recorded, either on a blank track provided for that purpose or over the deposition protocol track containing information that has already been read (and is therefore no longer necessary). If the deposition protocol information is overwritten by the monomer sequence information, more space will be available on the disk for cells.

Figure 6E:
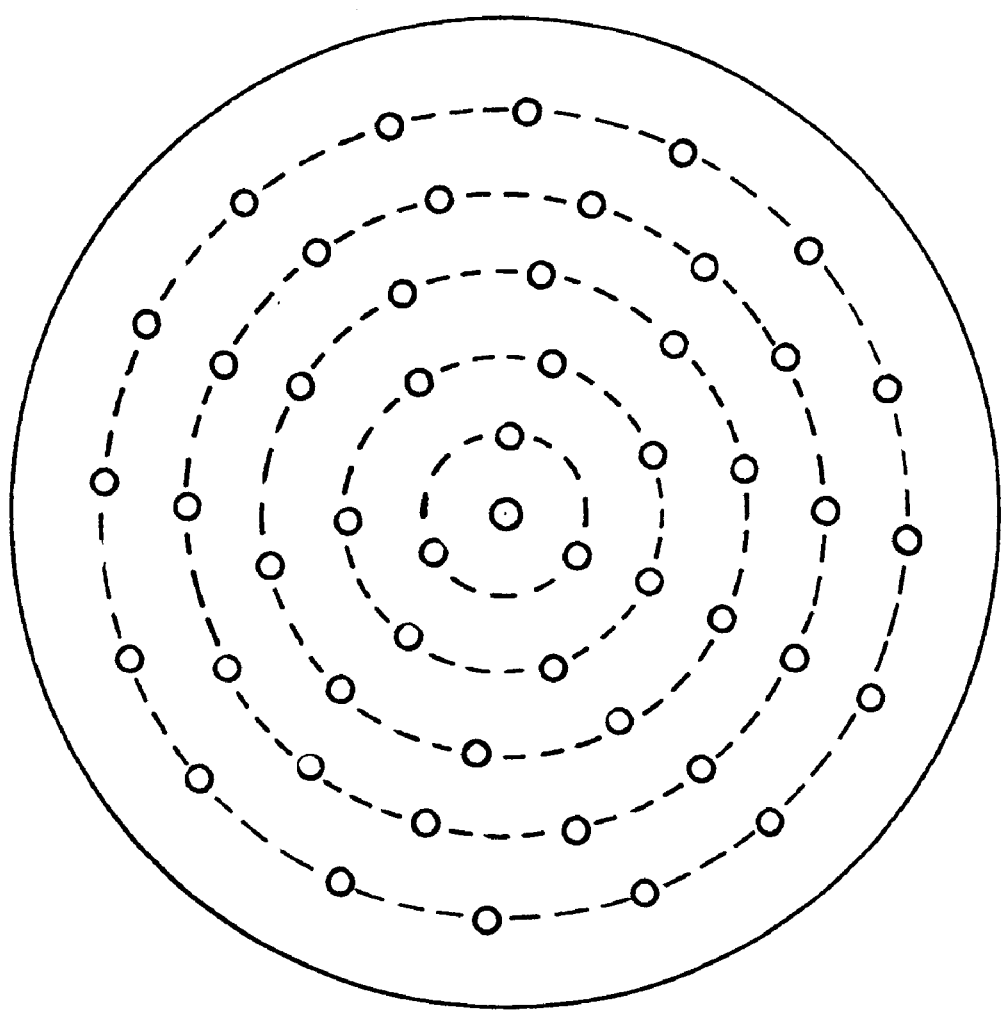

The above discussion has provided examples in which the information and cells were provided on different tracks, but they can be provided on the same track as shown in FIG. 6E. In this approach, less information needs to be read, stored, and interpreted between the successive deposition steps.

The arrangements shown in FIGS. 6A–6E can easily be adapted for use in a spiral rather than concentric format. If the read/write head and the dispenser travel together along the spiral, the deposition information can be read by the read/write head and almost immediately translated into deposition instructions for the dispenser. Of course, a short "phase lag" between the information track and the cell track is necessary to account for the information processing time. The lag can be provided by simply locating the cells slightly upstream from their corresponding deposition information. With this format, it is possible to quickly guide the dispenser for a single monomer along a track, stopping or slowing, if necessary, to deposit the monomer in the desired cells. This process can be repeated for each monomer dispenser, until all the cells are filled. After the polymerization reactions are conducted, the deposition process for the next layer of monomers is then started. Alternatively, each of several monomer dispensers can be used to deposit all of the necessary monomers during one traverse of the spiral track.

Disk operating systems have been designed to use the concentric format of magnetic disks. Therefore, a concentric optical disk format is preferable if the system is to be compatible with existing disk memories. The concentric format is also desirable when frequent multiple passes over the same track region are necessary. However, a spiral format requires less track jumping, thus speeding up the read/write process.

The disk tracks employed in the present invention can be divided into cell and information "sectors" analogous to the sectors in conventional magnetic and optical storage media. This allows the recorded material to be provided in standard size chunks that can be understood by conventional information processors. Further, in standard formats, sectors contain "header" information that allows the synthesizer to rapidly gain its "bearings" as it jumps from track to track seeking arbitrary cells or pieces of recorded information. The function and design of such headers is well-known in the optical and magnetic storage media arts, and discussed in, for example, Marchant, *Optical Recording*, Chapter 10, Addison-Wesley (1990), which was previously incorporated herein by reference for all purposes.

The amount of recording space needed to describe the monomer sequence of the polymer can be provided with a few bytes of data. The precise amount of data required is a function of the numbers of monomers in the longest polymer and the number of monomers in the basis set used to construct the polymer. If the basis set includes fewer than 256 monomers, a single byte can be used to identify each monomer in the polymer. If the basis set is larger, two bytes will serve to distinguish 65,536 different monomers. Of course, the entire sequence for each cell can be saved on the storage media, but this can be inefficient. In most instances, all sequences of a given sector or other unit are synthesized with some degree of redundancy, so that less data must be recorded for each cell. Thus, the header for a given sector might indicate that all cells within the sector contain specific isomers or derivatives of glucose, mannose, and ribose at the 2, 3, and 7 polymer positions, respectively. As described above, it is often efficient to use a deposition protocol in which a single monomer is deposited in a group of neighboring cells. Thus, it is expected that the polymer sets in many sectors will have the redundancy necessary to take advantage of the above recording strategy.

C. Accessing the Selected Cells

The synthesizer in this embodiment preferably employs one or more computerized servo motor systems to orient a given cell under the dispenser for a specified monomer, and to keep track of which monomers are applied to each cell. The read/write and dispenser head described above provides one structure for this purpose. An aliquot of the specified first monomer can be applied to cells 1, 101, 201, . . . to 9901, a second can be applied to cells 2, 102, 202 . . . to 9902, and so on for all the cells and monomers.

With only slight modifications, a conventional disk drive seeking method can be used to access a specific cell or group of cells from anywhere on the disk. Thus, if the track and sector of a cell are known, the read/write head and dispenser, if necessary, can be moved radially, counting the tracks crossed, until the desired track is located. After settling and confirming that the proper track has been reached, the synthesizer can be synchronized with the disk by reading the appropriate control information on the track. The appropriate sector and cell is then identified by reading the header information.

In some embodiments, the disk is moving continuously during the deposition step. By carefully controlling the disk speed and dispenser position, the monomer drops are expelled in short pulses, timed to correspond with the passage of particular cells under the dispenser head. The electrostatic control mechanisms described above helps guide the monomer-containing drops to their desired locations. To realize the full potential for polymer diversity in the present invention, some deposition steps must take place over different tracks and non-contiguous sectors. Thus, the monomer is deposited at various unrelated points over the disk surface. The disk rotates and stops at various angular positions, while the monomer dispenser jumps radially (or tangentially) to the location of the cell where the monomer is dispensed.

For many deposition steps, however, the system takes advantage of the disk's rotation to rapidly access the desired cells. Very rapid processing can be realized when some deposition steps deliver one monomer to all or most of the cells on a track of the disk. This greatly speeds the deposition process, as the dispenser does not have to move from a single radial position during deposition. Deposition in accordance with this approach is accomplished by first moving the dispenser radially an appropriate distance until it is positioned over the appropriate track, and then expelling metered amounts of the monomer solution for a sufficient period to cover the desired angular displacement on the disk.

The position of the dispenser can be moved across the rotatable disk by a variety of actuators. Typically, the dispenser is mounted on an arm that can be driven by voice-coil motors in conjunction with servo systems which sense position information from disks. Such actuators systems are commonly employed in magnetic hard disk drives. These are described in, for example, *Magnetic Recording* Vol. II, Chptr. 2 by C. D. Mee and E. D. Daniel, McGraw-Hill (1988), which is incorporated by reference herein for all purposes. If individual jets or capillaries for each reagent are involved, they can be individually positioned over the desired zones by sliding precisely along a track mounted on the arm.

D. Depositing Reactants in the Selected Cells

A variety of methods can be used to direct the monomer solutions from the reservoirs to the desired cells on the disk. As described above, micropipette, ink-jet, and pen plotter technologies are sufficiently developed and flexible to be useful in the present invention. In addition, electrophoretic and osmotic pumps, also described above, can be employed. These technologies are capable of delivering very small amounts of material to a selected location, thus permitting very small cells to be used in the present invention. The droplets produced by the dispensers of the present invention preferably range in diameter from about 200 $\mu$m to about 500 $\mu$m depending upon the application, although smaller sizes (to, for example, 50 $\mu$m) may be possible. As noted above, standard micropipettes can provide 4.6 nanoliter droplets having a diameter of approximately 0.21 mm. Droplet size can be controlled by a variety of methods well-known in the art. For example, the solution feed rate affects the drop size. In addition, pulsed electrical fields or vibrations at the nozzle (created by a piezoelectric pump, for example) affect the drop size.

In some embodiments, it will be desirable to charge the drops so that a controlled electric field can direct the droplets to the desired cells. Typically, the liquid will be stored in capillary tubes in which a charged electrode is present. Hence, the liquid surface will develop a charge. The liquid will therefore be drawn to a grounded substrate. When the capillary is charged to a few hundred volts, the liquid leaves in a fine stream of electrically charged droplets. If the capillary is charged to a few thousand volts, a jet of electrically charged liquid flies from the nozzle.

In some embodiments, there will be a charge on the nozzle of the dispenser to produce the electric field useful in guiding the droplets (or jet) to the substrate. Of course, other charged surfaces (such as plates or cylinders) can be placed near the path of the liquid to alter the electric field and hence the trajectory of the droplets. By carefully controlling the electric field in this manner, the deposition location of the monomer solution droplets can be tailored for the particular characteristics of the disk system.

Other means of charging the droplets can also be employed, such as, for example, standard "corona charging" methods. With these techniques, a stream of particles or drops passes through a corona discharge (a region where an intense electric field created by a sharply pointed and highly-charged electrode which ionizes the surrounding air molecules). When particles or droplets are passed through the corona discharge, they are bombarded by the ionized air molecules and they, themselves, receive a charge, thus permitting them to be guided by an electric field to the disk for deposition. Corona charging techniques do not require the use of an electrode, thereby avoiding a possible source of contamination in corrosive solutions. Related techniques are widely used to precipitate particulate emissions from power-station chimneys and other industrial plants, and to filter dust from air in offices and other public places.

After the monomer solution has been directed to the desired cell, it should remain there during subsequent processing steps until it is washed off the substrate. As mentioned above in the discussion with respect to the substrate, the cells may take the form of wells or dimples surrounded by a non-wetting coating. This helps to localize the monomers at the positions of the elements of the array, thus avoiding cross-reactions with the reactants in neighboring cells.

In some embodiments, especially optical-type read/record systems, a dimpled surface is unnecessary. As alluded to above, high surface tension liquids (and hydrophobic substrate coatings) can be employed to increase the surface forces that will tend to keep the reactant solutions in place. Of course, such properties are also desirable in dimpled systems, especially when the disk substrate is rotated at high speeds. As is well-known in the art, various inert materials can be added to the monomer solutions to control the surface tension, viscosity, and other physical properties of the monomer solutions.

E. Peptide Synthesis

The surface to which the reagents are to be applied is suitably derivatized, with a spacer molecule if necessary, in order to form covalent bonds with the applied monomers. Heat, catalyst (e.g., gaseous acid or base), etc. are subsequently supplied to the entire surface or to individual cells, as required by the coupling chemistry, so that the first monomers attach to the substrate. The surface is typically washed to remove unreacted reagent after the first round of monomers is bound. A second round of reagents is then squirted or otherwise deposited into predetermined cells and the disk surface is once again incubated at reaction conditions selected to minimize cleavage of the preceding covalent link and preserve the sequence of all the products. Solution phase polymerization of the monomers should be discouraged by, for example, preventing one end of each monomer from reacting. As described above, this can be accomplished by attaching a cleavable protecting group on a reactive end of the monomer.

The basic reaction strategy of Merrifield, described above, can be used in each cell of the disk. The particular chemical reagents used to effect the reactions can be any of those commonly used in the art, as discussed above.

Because many of the reactions can take place under similar conditions, it may be desirable to adjust the concentrations or ingredients (e.g., monomer or buffers) of the different reagent formulations to compensate for differences in reactivity or tendency to undergo side reactions. It is highly desirable to push every reaction to near quantitative conversion to minimize the development of deletion compounds. Capping the unreacted chains before deprotection can be employed to minimize the interference which such deletion compounds might introduce.

F. Imaging the Array

According to preferred embodiments, the array of polymer sequences is utilized in one or more of a variety of screening processes. For example, according to one embodiment, the entire disk substrate is exposed to a receptor of interest such as an enzyme or antibody. According to preferred embodiments, the receptor is labelled with fluorescein, or other detectable material, so as to provide for easy detection of the location(s) at which the receptor binds. According to still other embodiments, the binding signal is provided by exposing the substrate to the receptor of interest, and then exposing the substrate to a labelled material which is complementary to the receptor of interest and which preferably binds at multiple locations of the receptor of interest. For example, in one specific embodiment, if a mouse antibody is to be studied, a labelled second antibody can be exposed to the substrate which is, for example, goat-antimouse antibody. Such techniques are described in PCT Application WO/10092, previously incorporated herein by reference.

In addition to fluorescence, absorbance, ellipsometry, reflectance, and various types of spectroscopy may be used to study the various elements of the array. The entire array can be imaged by techniques well known in the art, including spot reading, spot scanning, and area imaging.

Conclusion

The above description is illustrative and not restrictive. Many variations of the invention will become apparent to those of skill in the art upon review of this disclosure. For example, although the substrate has been described as having cells on only two dimensions, it can have cells on three dimensions. Further, the bottom of a flat substrate, as well as the top, can be utilized in some arrays. Such a substrate would be analogous to the double sided magnetic storage disks in wide use today. These and other embodiments show that the scope of the invention should be determined not with reference to the above description, but instead with reference to the appended claims along with their full scope of equivalents.

What is claimed is:

1. A method for conducting a plurality of reactions on a substrate comprising at least one surface, said at least one surface comprising a plurality of cells at known locations, the location of each cell being encoded by information readable with an optical, electrical, magnetic or electromagnetic sensor, said method comprising:
    (a) selecting a first set of one or more cells on said at least one surface of said substrate;
    (b) decoding the locations of said first set of one or more cells by said sensor and delivering a first reactant to each cell of said first set of one or more cells;
    (c) selecting a second set of one or more cells on said at least one surface of said substrate;
    (d) decoding the locations of said second set of one or more cells by said sensor and delivering a second reactant to each cell of said second set of one or more cells; and
    (e) reacting said first reactant in each cell of said first set of one or more cells and said second reactant in each cell of said second set of one or more cells such that covalent bonds are formed with said surface, wherein the first reactant is prevented from contacting the second set of one or more cells and the second reactant is prevented from contacting the first set of one or more cells.

2. The method of claim 1 where said delivering the first reactant to each cell of the first set of one or more cells comprises:
    (a) identifying a reference mark on said at least one surface of the substrate;
    (b) moving a dispenser of said reactants a fixed distance and direction from said reference mark such that the dispenser is positioned approximately above a first cell of the first set of one or more cells;
    (c) delivering the first reactant to the first cell; and
    (d) repeating (b) and (c) for each remaining cell of the first set of one or more cells.

3. The method of claim 1 wherein the first and second reactants are receptors.

4. The method of claim 1 wherein said substrate is a rotatable disk, and said delivering a first reactant to each cell of said first set of one or more cells comprises:
    (a) moving a dispenser of said first reactant to the radial position of a first cell from said first set of one or more cells;
    (b) rotating of said substrate with respect to the dispenser such that the dispenser is positioned approximately above said first cell;
    (c) delivering said first reactant to said first cell;
    (d) repeating (a), (b), and (c) for each remaining cell of said first set of one or more cells.

5. The method of claim 1 wherein the first and second reactants are delivered to the cells from a micropipette.

6. The method of claim 1 wherein the first and second reactants are delivered in charged droplets from capillaries having electrodes attached thereto.

7. The method of claim 1 wherein the substrate has surface regions surrounding the plurality of cells, the surface regions having a hydrophobic surface.

8. The method of claim 1, wherein said substrate is a rotatable disk, and said delivering a second reactant to each cell of said second set of one or more cells comprises:

(a) moving a dispenser of said second reactant to the radial position of a first cell from said second set of one or more cells;

(b) rotating said substrate with respect to the dispenser such that the dispenser is positioned approximately above said first cell;

(c) delivering said second reactant to said first cell; and (d) repeating (a), (b), and (c) for each remaining cell of said second set of one or more cells.

9. The method of claim 1 wherein the first and second reactants are monomers.

10. The method of claim 9 wherein the monomers are selected from the group consisting of amino acids, nucleotides and saccharides.

11. A method for conducting a plurality of reactions on a substrate comprising at least one surface, said at least one surface comprising a plurality of cells at known locations, the method comprising:

(a) selecting a first set of one or more cells and a second set of one or more cells on said at least one surface of said substrate;

(b) delivering a solution of a first reactant to the first set of one or more cells and delivering a solution of a second reactant to the second set of one or more cells; and (c) conducting reactions of the first reactant in the first set of one or more cells and of the second reactant in the second set of one or more cells such that covalent bonds are formed with said surface;

wherein regions of the substrate surrounding the first set of one or more cells are covered with a layer of protecting groups that are non-wetting with respect to the solutions of the first and second reactants.

12. The method of claim 11 wherein delivering a solution of a first reactant to the first set of one or more cells comprises:

(a) identifying a reference mark on said at least one surface of the substrate;

(b) moving a dispenser of said first reactant a fixed distance and direction from said reference mark such that the dispenser is positioned approximately above a first cell of the first set of one or more cells;

(c) delivering said reactant to said first cell; and (d) repeating (a) and (b) for each remaining cell of the first set of one or more cells.

13. The method of claim 11 wherein the protecting groups are selected from the group consisting of alkyl silanes.

14. The method of claim 11, wherein said delivering a solution of a second reactant to the second set of one or more cells comprises:

(a) identifying a reference mark on said at least one surface of the substrate;

(b) moving a dispenser of said first reactant a fixed distance and direction from said reference mark such that the dispenser is positioned approximately above a first cell of the second set of one or more cells;

(c) delivering said reactant to said first cell; and (d) repeating (a) and (b) for each remaining cell of the second set of one ore more cells.

15. A method for conducting a plurality of reactions on a substrate, said method comprising:

(a) providing a substrate comprising at least one surface, said at least one surface comprising a plurality of cells at known locations, wherein each cell of the plurality of cells comprises an area for conducting a reaction and the location of each cell on said at least one surface of the substrate is encoded by information readable with an optical, electrical, magnetic or electromagnetic sensor;

(a) selecting a first set of one or more cells on the surface on the substrate;

(b) locating each cell of the first set of one or more cells by the sensor and delivering a first reactant to each cell of the first set of one or more cells;

(c) selecting a second set of one or more cells on the surface of the substrate;

(d) locating each cell of the second set of one or more cells by the sensor and delivering a second reactant to each cell of the second set of one or more cells; and (e) reacting the first reactant in each cell of the first set of one or more cells and the second reactant in each cell of the second set of one or more cells such that covalent bonds are formed with said surface, wherein the first reactant is prevented from contacting the second set of one or more cells and the second reactant is prevented from contacting the first set of one or more cells.

16. The method of claim 15, wherein the spacing between each cell of the first and second sets of one or more cells is 10 $\mu m^2$ or less.

17. The method of claim 15, wherein the area of each cell of the first and second sets of one or more cells is less than about 1 $mm^2$.

18. The method of claim 17, wherein the area of each cell of the first and second sets of one or more cells is between about 100 $\mu m^2$ and about 1 $mm^2$.

19. A method for conducting a plurality of reactions on a substrate comprising:

(a) providing a substrate comprising a magnetic or optical storage medium and a plurality of cells at known locations thereon, the location of each cell being encoded by information readable with an optical, electrical, magnetic or electromagnetic sensor;

(b) selecting a first set of one or more cells on the substrate;

(c) locating each cell of the first set of one or more cells by the sensor and delivering a first reactant to each cell of the first set of one or more cells;

(d) selecting a second set of one or more cells on the substrate;

(e) locating each cell of the second set of one or more cells by the sensor and delivering a second reactant to each cell of the second set of one or more cells; and (f) reacting the first reactant in each cell of the first set of one or more cells and the second reactant in each cell of the second set of one or more cells such that covalent bonds are formed with said surface, wherein the first reactant is prevented from contacting the second set of one or more cells and the second reactant is prevented from contacting the first set of one or more cells.

20. The method of claim 19, wherein the substrate is an optical or magnetic storage disk.

* * * * *